United States Patent
Courtney et al.

(10) Patent No.: US 9,076,202 B2
(45) Date of Patent: Jul. 7, 2015

(54) SYSTEMS AND METHODS FOR IMPROVED VISUALIZATION DURING MINIMALLY INVASIVE PROCEDURES

(75) Inventors: Brian Courtney, Toronto (CA); Amandeep Thind, Toronto (CA)

(73) Assignee: COLIBRI TECHNOLOGIES INC., North York, ON (CA)

(*) Notice: Subject to any disclaimer, the term of this patent is extended or adjusted under 35 U.S.C. 154(b) by 146 days.

(21) Appl. No.: 13/509,982

(22) PCT Filed: Nov. 8, 2011

(86) PCT No.: PCT/CA2011/050693
§ 371 (c)(1),
(2), (4) Date: Aug. 24, 2012

(87) PCT Pub. No.: WO2012/061940
PCT Pub. Date: May 18, 2012

(65) Prior Publication Data
US 2013/0216114 A1    Aug. 22, 2013

Related U.S. Application Data

(60) Provisional application No. 61/411,225, filed on Nov. 8, 2010.

(51) Int. Cl.
G06K 9/00    (2006.01)
G06T 7/00    (2006.01)
(Continued)

(52) U.S. Cl.
CPC ............ *G06T 7/0026* (2013.01); *A61B 5/0066* (2013.01); *A61B 5/6852* (2013.01);
(Continued)

(58) Field of Classification Search
CPC ....... G06F 19/34; G06F 19/3437; A61B 1/00; A61B 1/00002; A61B 1/041; A61B 5/0066; A61B 5/0084; A61B 5/0402; A61B 5/065; A61B 5/6852; A61B 5/6876; A61B 5/7264; A61B 8/12; A61B 8/4245; A61B 8/4416; A61B 8/445; A61B 18/24; A61B 2019/5289; G06T 7/0012; G06T 2207/10048; G06T 2207/10101; G06T 2207/10132; G06T 2207/30101; G06T 2207/30004; G06T 2207/30021; G06T 2207/30024; G06T 2207/30028
See application file for complete search history.

(56) References Cited

U.S. PATENT DOCUMENTS 4,794,931 A    1/1989 Yock
5,203,337 A *  4/1993 Feldman ................... 600/463
(Continued)

FOREIGN PATENT DOCUMENTS

WO    2006121851    11/2006

*Primary Examiner* — Manav Seth
(74) *Attorney, Agent, or Firm* — Lynn C. Schumacher; Stephen W. Leonard; Hill & Schumacher

(57) ABSTRACT

Systems and methods are provided for performing a minimally invasive procedure in an automated or semi-automated fashion, where an imaging probe having an imaging modality compatible with the presence of an intraluminal medium is employed to record images that are processed to identify regions of interest and direct a medium displacement operation during a subsequent minimally invasive operation that benefits from the displacement of the intraluminal medium. The minimally invasive operation may include recording images with a second imaging modality, or may be a therapeutic treatment. The method is may be performed in real-time, where images obtained from the first imaging modality are processed in real time to determine whether or not the minimally invasive operation is to be performed at a given position.

128 Claims, 9 Drawing Sheets

(51) Int. Cl.
  *A61B 8/12* (2006.01)
  *A61B 5/06* (2006.01)
  *A61B 5/00* (2006.01)
  *A61B 8/00* (2006.01)
  *A61B 5/0402* (2006.01)
  *A61B 18/24* (2006.01)
  *A61B 19/00* (2006.01)

(52) U.S. Cl.
  CPC .............. *A61B 5/6876* (2013.01); *A61B 8/12* (2013.01); *A61B 8/4245* (2013.01); *A61B 8/4416* (2013.01); *A61B 5/0084* (2013.01); *A61B 5/0402* (2013.01); *A61B 5/065* (2013.01); *A61B 18/24* (2013.01); *A61B 2019/5289* (2013.01); *G06T 7/0012* (2013.01); *G06T 2207/10048* (2013.01); *G06T 2207/10101* (2013.01); *G06T 2207/10132* (2013.01); *G06T 2207/30101* (2013.01); *A61B 5/7264* (2013.01); *A61B 8/445* (2013.01)

(56) References Cited

U.S. PATENT DOCUMENTS

| | | |
|---|---|---|
| 5,718,231 A | 2/1998 | Dewhurst et al. |
| 5,722,403 A | 3/1998 | McGee et al. |
| 5,740,808 A | 4/1998 | Panescu et al. |
| 5,752,158 A | 5/1998 | Stephenson et al. |
| 5,752,518 A | 5/1998 | McGee et al. |
| 5,848,969 A | 12/1998 | Panescu et al. |
| 5,904,651 A | 5/1999 | Swanson et al. |
| 6,019,724 A * | 2/2000 | Gronningsaeter et al. .... 600/439 |
| 6,047,218 A | 4/2000 | Whayne et al. |
| 6,066,096 A * | 5/2000 | Smith et al. ................... 600/439 |
| 6,134,003 A | 10/2000 | Tearney et al. |
| 6,178,346 B1 | 1/2001 | Amundson et al. |
| 6,200,268 B1 | 3/2001 | Vince et al. |
| 6,390,978 B1 | 5/2002 | Irion et al. |
| 6,530,888 B2 * | 3/2003 | Smith et al. ................... 600/463 |
| 6,572,551 B1 * | 6/2003 | Smith et al. ................... 600/459 |
| 7,074,179 B2 * | 7/2006 | Wang et al. .................... 600/101 |
| 7,074,187 B2 * | 7/2006 | Selzer et al. ................... 600/440 |
| 7,289,842 B2 | 10/2007 | Maschke |
| 7,312,879 B2 * | 12/2007 | Johnston ....................... 356/614 |
| 7,352,339 B2 | 4/2008 | Morgan et al. |
| 7,510,536 B2 * | 3/2009 | Foley et al. ....................... 601/2 |
| 7,618,371 B2 * | 11/2009 | Younge et al. ................ 600/439 |
| 7,620,220 B2 * | 11/2009 | Lam .............................. 382/128 |
| 7,625,366 B2 | 12/2009 | Atlas |
| 7,674,240 B2 | 3/2010 | Webler et al. |
| 7,747,315 B2 | 6/2010 | Villard |
| 7,758,499 B2 | 7/2010 | Adler |
| 7,794,446 B2 | 9/2010 | Boese et al. |
| 7,935,059 B2 * | 5/2011 | Younge et al. ................ 600/443 |
| 2006/0116571 A1 | 6/2006 | Maschke et al. |
| 2007/0135803 A1 | 6/2007 | Belson |
| 2008/0177138 A1 | 7/2008 | Courtney et al. |
| 2009/0299195 A1 | 12/2009 | Muller et al. |

* cited by examiner

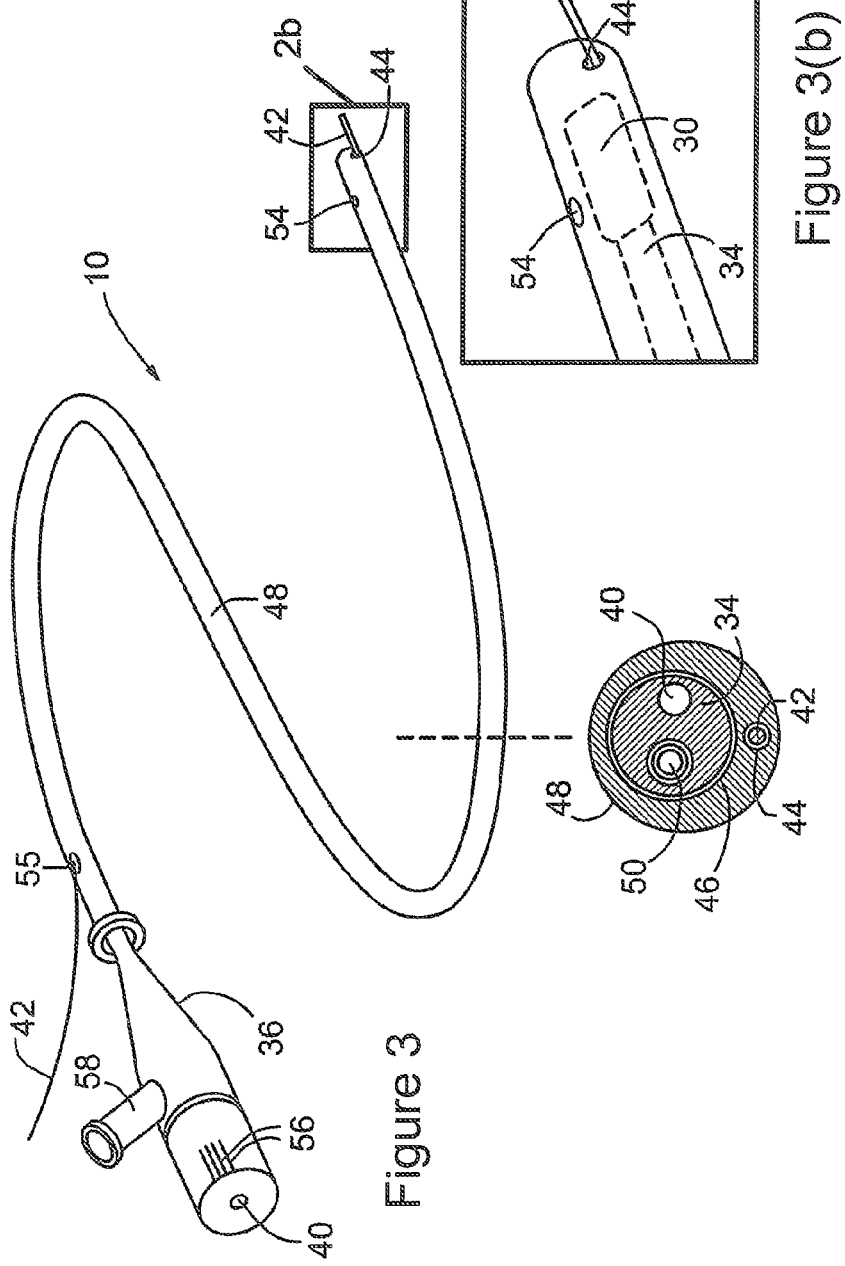

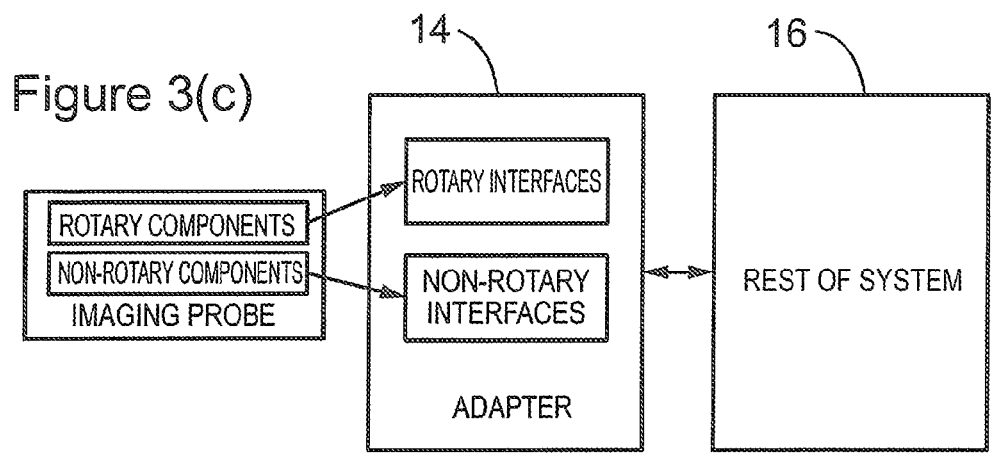
Figure 3(c)
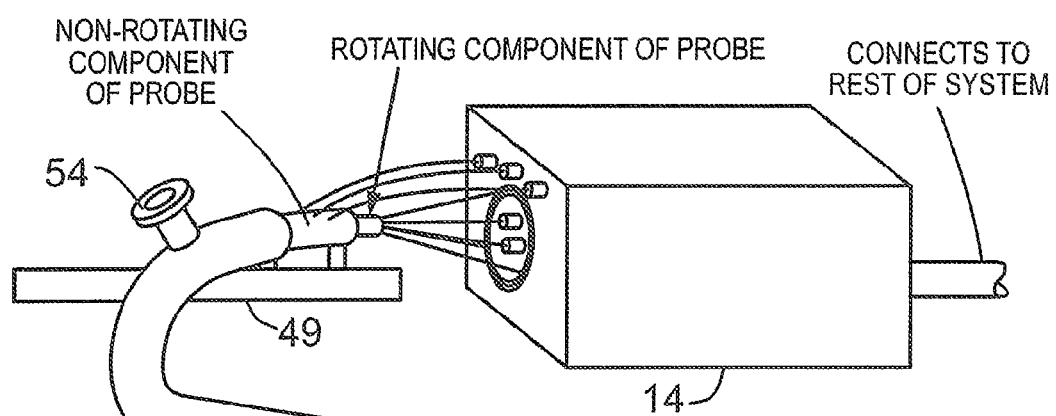
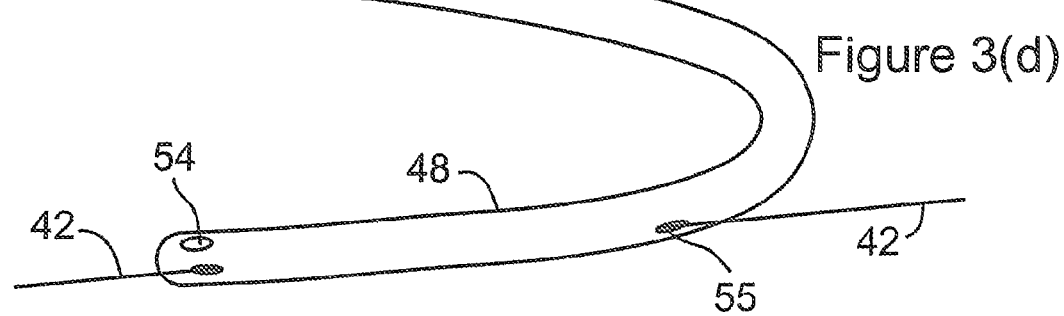
Figure 3(d)
PRIOR ART

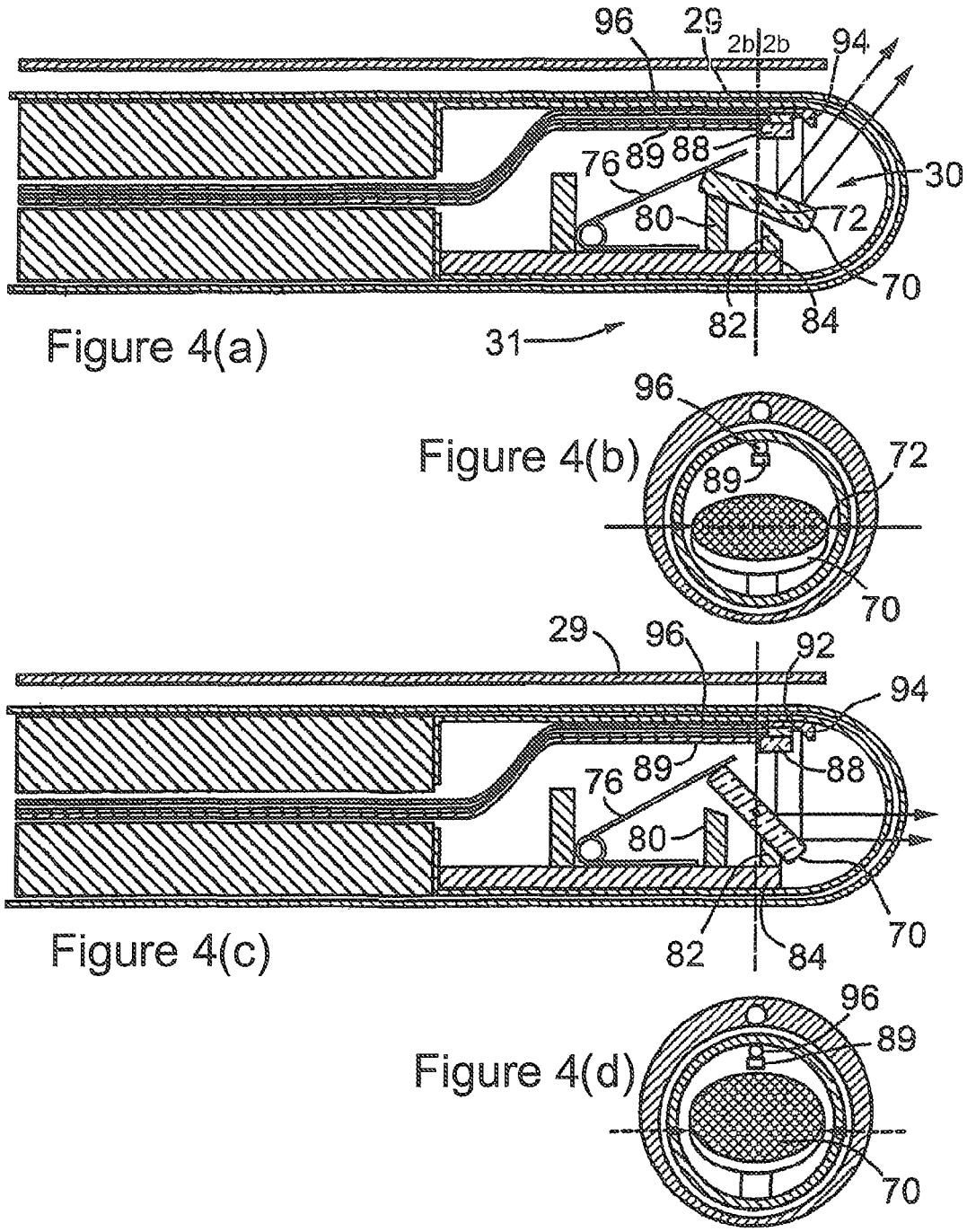
PRIOR ART

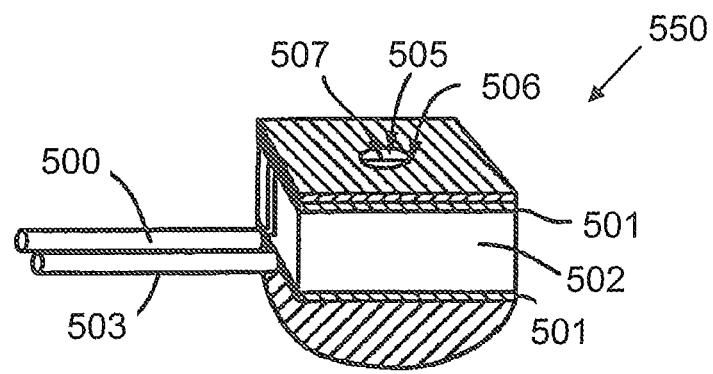
(a)
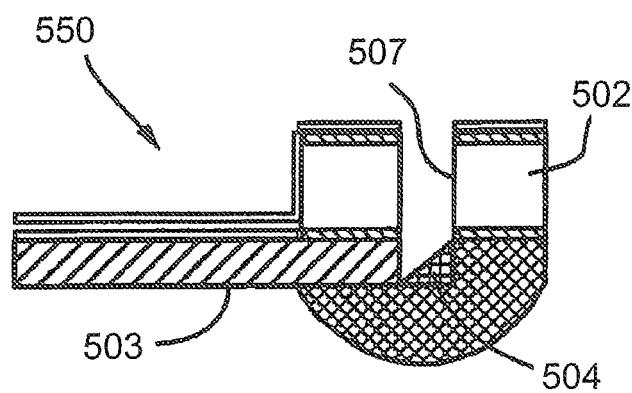
(b)
PRIOR ART
Figure 5

SYSTEMS AND METHODS FOR IMPROVED VISUALIZATION DURING MINIMALLY INVASIVE PROCEDURES

CROSS-REFERENCE TO RELATED APPLICATION

This application is a National Phase application claiming the benefit of PCT/CA2011/050693 filed on Nov. 8, 2011, in English, which further claims priority to U.S. Provisional Application No. 61/411,225, titled "SYSTEMS AND METHODS FOR IMPROVED VISUALIZATION DURING MINIMALLY INVASIVE PROCEDURES" and filed on Nov. 8, 2010, the entire contents of which are incorporated herein by reference.

BACKGROUND

The present disclosure relates generally to the field of high resolution medical imaging. More particularly, the present disclosure relates to minimally invasive methods involving two or more imaging modalities.

High resolution medical imaging has broad diagnostic utility, including assessing tissue structures, anatomy and/or composition, planning and/or guiding interventions on localized regions of the body, and assessing the result of interventions that alter the structure, composition or other properties of the localized region. Among the many different high resolution imaging modalities, high frequency ultrasound and optical coherence tomography are two highly useful clinical and research tools.

High frequency ultrasound is a technique that is particularly useful for intravascular and intracardiac procedures. For these applications, one or more ultrasound transducers are incorporated into a catheter or other device that can be inserted into the body. Two particularly important implementations of high frequency ultrasound are intravascular ultrasound (IVUS), for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

The center frequency of IVUS typically lies within the range of 3 to 200 MHz and more typically in the range of 8 to 80 MHz. Higher frequencies provide higher resolution but result in worse signal penetration and thus a smaller field of view. Depth of penetration can range from less than a millimeter to several centimeters depending on several parameters such as center frequency and geometry of the transducer, the attenuation of the media through which the imaging occurs and implementation-specific specifications that affect the signal to noise ratio of the system.

High resolution imaging methods often involve the use of a rotary shaft to transmit torque to an imaging device near the distal end of the probe. These rotary shafts are often long, thin and flexible so that they can be delivered through anatomical conduits, such as the vasculature, genitourinary tracts, respiratory tracts and other such bodily lumens. Ideally, when torque is applied to the cable in a specified direction the torque cable develops a property of having a close relation between the degree of rotation at its proximal and distal ends. This allows the simplification of the design of an ultrasound catheter by making the angle of rotation at the distal end of the torque cable (within the body) a reasonable approximation of the angle of rotation at the proximal end of the torque cable (outside of the body).

Other imaging systems operate without a torque cable, such as angioscopy catheters (which employ fiber optic bundles) and phased array imaging systems. Additionally, imaging systems have been proposed and demonstrated that incorporate a micro-motor in the distal end of the catheter instead of relying on a torque cable.

Variations of high frequency ultrasound exist, where the signal acquisition and/or analysis of the backscattered signal is modified to facilitate obtaining or inferring further information about the imaged tissue. These include elastography, where the strain within tissue is assessed as the tissue is compressed at different blood pressures (de Korte et al Circulation. 2002 Apr. 9; 105(14):1627-30); Doppler imaging which assesses motion such as blood flow within anatomic structures; virtual histology, which attempts to infer the composition of tissue using the radio-frequency properties of the backscattered signal combined with a pattern recognition algorithm (Nair, U.S. Pat. No. 6,200,268); second harmonic imaging (Goertz et al, Invest Radiol. 2006 August; 41(8):631-8) and others. Ultrasound transducers are improving considerably, including the use of single crystal ultrasound transducers and composite ultrasound transducers.

A catheter-based system for intravascular ultrasound is described by Yock (U.S. Pat. No. 4,794,931) to provide high resolution imaging of structures in blood vessels. This system comprises an outer sheath, within which there is an ultrasound transducer near the distal end of a long torque cable. When a motor rotates the torque cable and ultrasound transducer assembly, 2D cross-sectional images of anatomical structures, such as blood vessels, can be made. Linear translation of the catheter or the torque cable and ultrasound transducer in combination with the rotational motion of the ultrasound transducer allows for acquisition of a series of 2D images along the length of the catheter.

Hossack et al (WO/2006/121851) describe a forward looking ultrasound transducer using a CMUT transducer and a reflective surface.

Optical imaging methods based on fiber optic technology used in the field of medicine include optical coherence tomography (OCT), angioscopy, near infrared spectroscopy, Raman spectroscopy and fluorescence spectroscopy. These modalities typically require the use of one or more optical fibers to transmit light energy along a shaft between an imaging site and an imaging detector.

Optical coherence tomography is an optical analog of ultrasound, and provides imaging resolutions on the order of 1 to 30 microns, but does not penetrate as deeply into tissue as ultrasound in most cases. Fiber optics can also be used to deliver energy for therapeutic maneuvers such as laser ablation of tissue and photodynamic therapy. Other useful optical imaging modalities include endoscopy and other similar or related imaging mechanisms that involve the use of a probe to obtain images based on the back-reflection of light. Miniaturization of detectors and light sources is making it possible to include the light sources and/or detectors in the catheter itself, potentially obviating the need for fiber optics to act as an intermediary component in the transmission and/or detection of light.

Optical coherence tomography is limited by its small penetration depth (on the order of 500 to 3000 microns) in most biologic media. Most such media, including blood, are not optically transparent. OCT has thus far required the displacement of blood to create an optically clear environment for this purpose. One approach is to displace the blood with another fluid prior to performing measurements with the imaging modality incompatible with blood. U.S. Pat. No. 7,625,366, issued to Atlas, provides an exemplary flush catheter for injecting a flush solution into a vessel for performing OCT measurements with minimal blood displacement. Fluids that have been either used or contemplated for this purpose include radio-opaque contrast or various formulations of saline, Ringer's lactate and others. U.S. Pat. No. 7,794,446 (issued to Bosse et al.) and U.S. Pat. No. 7,747,315 (issued to Villard et al.) disclose improved flush solution compositions for use in OCT imaging.

Displacement of blood by the introduction of another fluid with greater transparency provides a time interval in which optical coherence tomography imaging can occur. This time window can be extended by reducing the flow within the vessel, such as by the use guide catheters that incorporate an occlusion balloon. For example, U.S. Pat. Nos. 5,722,403, 5,740,808, 5,752,158, 5,848,969, 5,904,651, and 6,047,218, issued to McGee et al., provide imaging catheter systems including an inflatable balloon that incorporates an imaging apparatus. U.S. Pat. No. 7,674,240, issued to Webler et al., provides improved devices for inflating and deflating balloons for occluding a vessel.

Displacement of blood by means of introduction of another fluid to improve OCT imaging is conventionally done by a manual process, where the operator injects the transparent fluid on one or more occasions during an imaging procedure. Such injection may be done via a number of methods, including use of a manual syringe, use of pressurized fluid delivery systems and use of powered pumps. Pressurized fluid delivery systems can include the simple use of gravitational forces to provide pressure, as well as devices that apply pressure to a compressible or deformable compartment filled with the fluid of interest. For example, pressure infuser bags use an inflatable bladder, similar to that of a conventional blood pressure cuff, to apply pressure to a bag of fluid within a confined compartment. The inflatable bladder and the bag of fluid share a confined space. Therefore, when the bladder is inflated, such as with a manual hand pump, pressurized infusions of fluid into a patient is possible.

Alternatively, blood can be displaced by use of a balloon filled with an optically clear medium, such as radio-opaque contrast, saline or air. The balloon may surround the region of the catheter where light, such as that used for OCT imaging or near infra-red (NIR) spectroscopy, exits the imaging probe.

Unfortunately, complications can arise when displacing blood from a vessel. For example, there is a small risk of embolic events, if the introduction of displaced fluid dislodges particles from the vessel wall. There is a risk of causing or worsening a dissection between the layers of the vessel wall if fluid is injected inadvertently with too much force, or if the fluid is injected near a pre-existing dissection site. In critical organs such as the heart, the potential complications of displacing blood with another fluid include ischemia to the target organ and arrhythmias. Cardiac arrhythmias may occur as a result of hypoxia if the displacing fluid does not carry adequate oxygen to the myocardium. They may also occur due to changes in the concentrations of electrolytes in the myocardium.

For vessels that perfuse critical organs sensitive to hypoxia, such as the heart, brain and kidneys, prolonged intervals of blood displacement and/or vascular occlusion can lead to adverse clinical events, and the operator may be compelled to minimize the duration of time over which the displacement of blood occurs.

The need to minimize the amount of time during which blood is displaced has to be balanced with the desire to acquire an adequate amount of imaging data. For example, if the imaging probe is translated along the vessel's longitudinal axis, the portion of the vessel adequately imaged by an optical imaging technique will be limited by the length of time during which blood is displaced adequately. Not only is the time duration over which blood is displaced of importance, but if an injection of an optically transmissive fluid is being used, then the volume of fluid injected may have important consequences. For example, some operators use radio-opaque contrast as the optically transmissive medium. Yet it is well known in the field of medicine that contrast agents frequently have deleterious effects on kidney function and can contribute to acute renal failure. Conversely, inadequate displacement of blood results in sub-optimal imaging.

Variations of optical coherence tomography (OCT) include polarization sensitive OCT (PS-OCT) where the birefringent properties of tissue components can be exploited to obtain additional information about structure and composition; spectroscopic OCT which similarly provides improved information regarding the composition of the imaged structures; Doppler OCT which provides information regarding flow and motion; elastography via OCT; and optical frequency domain imaging (OFDI), which allows for a markedly more rapid acquisition of imaging data and therefore enables imaging to occur over a larger volume of interest in less time.

There exist several other forms of fiber-optic based imaging other than OCT. Amundson et al describe a system for imaging through blood using infrared light (U.S. Pat. No. 6,178,346). The range of the electromagnetic spectrum that is used for their imaging system is selected to be one which optimizes penetration through blood, allowing optical imaging through blood similar to that afforded by angioscopy in the visible spectrum, but without the need to flush blood away from the region being imaged.

Tearney et al (U.S. Pat. No. 6,134,003) describe several embodiments that enable optical coherence tomography to provide higher resolution imaging than is readily obtained by high frequency ultrasound or IVUS.

Dewhurst (U.S. Pat. No. 5,718,231) discloses a forward looking probe for intravascular imaging where a fiber optic travels through an ultrasound transducer to shine light on a target tissue straight in front of the end of the probe. The light then interacts with the target tissue and makes ultrasound waves, which are received by the ultrasound sensor and the images are photoacoustic images only as the system is not configured to receive and process optical images. The ultrasound sensor used in the Dewhurst device is limited to thin film polymeric piezoelectrics, such as thin film PVDF, and is used only to receive ultrasound energy, not to convert electrical energy to ultrasound.

Angioscopy, endoscopy, bronchoscopy and many other imaging devices have been described which allow for the visualization of internal conduits and structures (such as vessels, gastrointestinal lumens and the pulmonary system) in mammalian bodies based on the principle of illuminating a region within the body near the distal end of a rigid or flexible shaft. Images are then created by either having a photodetector array (such as a CCD array) near the end of the shaft or by having a bundle of fiber optics transmit the received light from the distal end of the shaft to the proximal end where a photodetector array or other system that allows the operator to generate or look at an image representative of the illuminated region. Fiber bundles are bulky and reduce the flexibility of the shaft among other disadvantages.

Other fiber optic based modalities for minimally invasive assessment of anatomic structures include Raman spectroscopy as described by Motz et al. (J Biomed Opt. 2006 March-April; 11(2)), near infrared spectroscopy as described by Caplan et al (J Am Coll Cardiol. 2006 Apr. 18; 47(8 Suppl):

C92-6) and fluorescence imaging, such as tagged fluorescent imaging of proteolytic enzymes in tumors (Radiology. 2004 June; 231(3):659-66).

Recently, probe designs have emerged that combine multiple imaging modalities in a single device. Maschke (United States Patent Publication No. 2006/0116571 corresponding to U.S. patent application Ser. No. 11/291,593) describes an embodiment of a guidewire with both OCT and IVUS imaging transducers mounted upon it. The described invention has several shortcomings. Guidewires are typically 0.014" to 0.035" in diameter (approximately 350 microns to 875 microns), yet ultrasound transducers typically are at least 400 microns×400 microns and generally are larger in size for the frequencies in the 20 to 100 MHz range. If the transducer is too small, the beam is poorly focused and has poor signal properties. In Maschke, the IVUS and OCT imaging mechanisms are located at different positions along the length of the guidewire, and a substantial drawback associated with this type of configuration (having the IVUS and OCT imaging means located at different positions along the length of an imaging shaft) is that optimal co-registration of images is not possible.

Similarly, U.S. Pat. No. 7,289,842 issued to Maschke describes an imaging system that combines IVUS and OCT on a catheter where the IVUS and OCT imaging elements are longitudinally displaced from each other along the length of a catheter that rotates around its longitudinal axis. Maschke also describes generating images where the center portion of the images are substantially derived from the output of the higher resolution OCT imaging portion of the system while the outer portion of the images are substantially derived from the output of the ultrasound imaging portion of the system, to make use of ultrasound's greater depth of penetration in combination with OCT's higher resolution for tissues close to the catheter.

U.S. Pat. No. 6,390,978, issued to Irion, describes the use of high frequency ultrasound in combination with optical coherence tomography where the ultrasound beam and the OCT beam are superimposed on each other.

In U.S. Patent Application Publication No. 2008/0177138, Courtney et al. provide an improved multimodal imaging system incorporating both IVUS and OCT transducers in a compact imaging assembly capable of side-viewing and/or forward-looking imaging. Such multimodal imaging systems offer the ability to obtain far greater diagnostic information than using a single modality imaging device. Indeed, optical coherence tomography generally has superior resolution to ultrasound and has the potential to better identify some structures or components in vascular and other tissues than ultrasound. For example, fibrous cap thickness or the presence of inflammatory or necrotic regions near the surface of arteries may be better resolved with optical coherence tomography.

Unfortunately, many multimodal imaging devices suffer from problems related to incompatibility of one or more imaging modalities with blood. For example, in the case of a multimodal imaging device combining both IVUS and OCT, the IVUS transducer is capable of functioning with the presence of blood in the vessel under investigation, but the OCT modality requires blood displacement. Such a requirement leads to complexity of operation and difficulties in coordinating and referencing the results from the two imaging modalities.

Another problem with the use of multimodal imaging devices is the inaccuracies in co-registration that might result when one imaging modality is used, followed by another imaging modality after blood displacement. For example, intravascular imaging, such as IVUS and OCT, is often used for clinical trial purposes where an imaging protocol is required. Manually using one or more modalities to identify regions that should be assessed in greater detail by one or more other modality is subject to a substantial amount of operator variability. Furthermore, clinical studies that depend on the ability to compare the structure and/or composition of vessels between different patients or at different time points will be dependent on reproducible methods for assessment.

In U.S. Pat. No. 7,758,499, Adler teaches the use of IR imaging with wavelengths of less than 1000 nm, which is minimally compromised by the presence of blood, in combination with other imaging modalities, such as imaging with visible light. To achieve multimodal optical imaging, blood displacement methods are employed, enabling imaging with IR and/or visible light.

The use of multiple imaging modalities in a single imaging device was also recently described by Muller et al. (US Patent Application Publication No. 2009/0299195). Muller describes methods and systems for combining intravascular ultrasound, optical coherence tomography, and near infrared spectroscopy for the detection of multiple, different abnormalities in the arterial morphology during a single intravascular procedure.

Unfortunately, the known methods employing manual operations for serially acquiring multimodal images require considerable skill and further involve complex image spatial alignment operations. Accordingly, there remains a need for multimodal imaging methods that address the aforementioned problems, enable standardized image data acquisition, and provide improved performance and clinical utility.

SUMMARY

Embodiments of the present disclosure provide systems and methods for improving the ability to identify and/or collect data from vessels and other tissues with intraluminal probes capable of collecting data using two or more imaging modalities, where one or more imaging modalities are capable of collecting data through an intraluminal medium (such as blood) and one or more other modalities function with improved performance when the intraluminal medium is at least partially displaced from the field of view.

In one aspect, there is provided a method of directing a medium displacement operation for performing a minimally invasive procedure within a lumen or cavity, the method comprising the steps of: recording a first set of images obtained from a first imaging modality when a first translation operation of a functional component of an imaging probe is performed; spatially correlating the first set of images with an associated position of the functional component of the imaging probe, wherein the first imaging modality is compatible with a presence of a displaceable medium; processing the first set of images and identifying a region of interest; and directing a medium displacement operation while a second translation operation of the functional component of the imaging probe is performed over the region of interest; wherein the minimally invasive procedure is performed within the region of interest during the medium displacement operation.

In another aspect, there is provided a method of directing a medium displacement operation for performing a minimally invasive imaging procedure within a lumen or cavity, the method comprising the steps of: a) obtaining one or more images from a first imaging modality of an imaging probe, wherein the first imaging modality is compatible with a presence of a displaceable medium; b) processing the one or more images to identify a region of interest; and c) if a region of interest is identified, directing a medium displacement operation and performing a minimally invasive procedure while the medium displacement operation is performed.

In another aspect, there is provided a method of directing a medium displacement operation for performing a minimally invasive procedure within a lumen or cavity with a probe, the method comprising the steps of: obtaining, with an external imaging apparatus, one or more images of a region within which the minimally invasive procedure is to be performed; identifying a region of interest within the one or more images; translating a functional component of the probe to the region of interest while obtaining one or more additional images with the external imaging apparatus, wherein a position of the functional component is identifiable in the one or more additional images; and directing a medium displacement operation while performing a translation operation associated with the functional component of the probe within the region of interest.

In another aspect, there is provided a method of directing a medium displacement operation for performing a minimally invasive procedure within a lumen or cavity, the method comprising the steps of: recording a set of measurements obtained from a non-imaging modality when a first translation operation of a functional component of a probe is performed; spatially correlating the set of measurements with an associated position of the functional component of the probe, wherein the non-imaging modality is compatible with a presence of a displaceable medium; processing the set of measurements and identifying a region of interest; and directing a medium displacement operation while a second translation operation of the functional component of the probe is performed over the region of interest; wherein the minimally invasive procedure is performed within the region of interest during the medium displacement operation.

In another aspect, there is provided a method of directing a medium displacement operation for performing a minimally invasive imaging procedure within a lumen or cavity, the method comprising the steps of: a) obtaining one or more measurements from a non-imaging modality of a probe, wherein the non-imaging modality is compatible with a presence of a displaceable medium; b) processing the one or more measurements to identify a region of interest; and c) if a region of interest is identified, directing a medium displacement operation and performing a minimally invasive procedure while the medium displacement operation is performed.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 3 is a perspective drawing showing an example of a multimodal imaging system incorporating both intravascular ultrasound (IVUS) and optical coherence tomography (OCT), showing a flexible imaging probe with a connector, conduit and imaging assembly;

FIG. 3(a) is a cross sectional view of the mid-section of the imaging probe of FIG. 1 taken along the dotted line;

FIG. 3(b) is an expanded perspective drawing of the distal region of the imaging probe of FIG. 1;

FIG. 3(c) shows a schematic of how the rotary and non-rotary components of the imaging probe can be coupled with an adapter to the rest of an imaging system.

FIG. 3(d) is a perspective drawing of an example of the coupling of the rotary and non-rotary components of the probe to an adapter.

FIG. 4(a)-(d) illustrates the distal end of an imaging probe that is capable of both acoustic and optical imaging where a tiltable deflecting surface can change the imaging angle as a function of the rotational velocity of the imaging assembly.

FIGS. 5 (a) and (b) illustrates an example of a side-viewing multimodal imaging assembly comprising an ultrasound transducer and an optical fiber for combined co-planar IVUS and OCT imaging.

DETAILED DESCRIPTION

Figure 1:
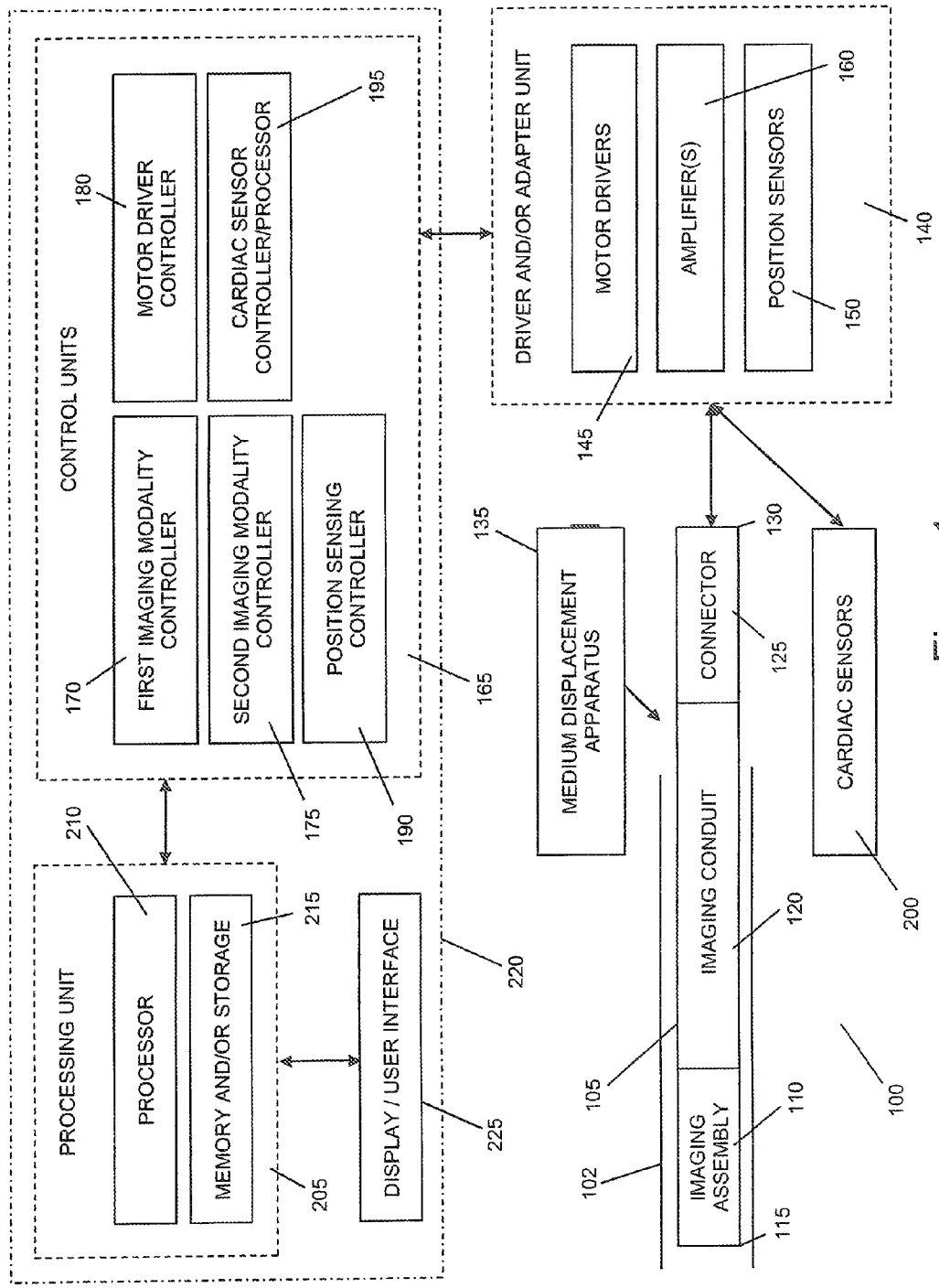
FIG. 1 is a block diagram illustrating a system for performing multimodal imaging.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "high resolution imaging" refers to high resolution imaging methods including, but not limited to, ultrasound and optical imaging. "High frequency ultrasound" as used herein refers to ultrasound imaging with frequencies of greater than about 3 MHz, and more typically in the range of 8 to 200 MHz.

As used herein, the term "imaging energy" refers to light or acoustic energy or both. Specifically, "light" and/or "optical" refers to electromagnetic waves with one or more wavelengths that may reside within in the ultraviolet, visible, near infra-red and/or infrared spectrum.

As used herein, the term "image analysis", generally refers to the processing of image data to identify regions of interest, where the regions of interest general pertain to one or more images or portions thereof that may be of relevance.

As used herein, the terms "translation" and "translation operation", when associated with an intraluminal probe such as an imaging probe, refer to the translation of at least a portion of the probe, such that a functional portion of the probe is translated relative to a lumen in which the probe is located. An example of a functional portion of a probe is an imaging assembly. A translation operation may involve translating a functional portion of a probe relative to another portion of a probe, such as an external sheath.

Embodiments of the present disclosure provide systems and methods for performing improved imaging during a minimally invasive procedure using a multimodal imaging catheter-based device for which least one imaging modality benefits from the displacement of intraluminal fluid during imaging. Specific embodiments provide standardized and/or automated systems and methods for selecting regions within a lumen for a subsequent imaging step involving the displacement of an intraluminal medium.

In one embodiment, a multimodal imaging system is provided that includes at least one imaging modality compatible with imaging in an intraluminal medium, and at least one imaging modality for which imaging performance is improved following the displacement of the intraluminal medium. Referring to FIG. 1, a block diagram is shown illustrating an example embodiment of a multimodal imaging system 100. The imaging probe 105, which is contained within a lumen that is deliverable to an anatomic structure 102 (for example, a lumen or blood vessel), includes an imaging assembly 110 near its distal end 115, an optional imaging conduit 120 along a substantial portion of its length, and a connector 125 at its proximal end 130.

Imaging assembly 110 generally refers to the component of the imaging probe 105 from which the multimodal signals (for example, acoustic and optical) are transmitted and/or collected when imaging a region that is proximate to the imaging assembly 110. Multimodal imaging assembly 110 includes components and devices for imaging using two or more imaging modalities. Imaging assembly 110 may include imaging transducers, detectors, and/or imaging energy coupling devices. Imaging energy for irradiating tissue in the vicinity of the probe according to a given imaging modality may be produced by one or more transducers housed within imaging assembly 110, and/or may be produced external to the imaging probe by one or more external transducers and delivered through an energy guiding device (such as a fiber optic or optical waveguide) through the imaging conduit 120 to imaging assembly 110. Similarly, incident imaging energy produced or scattered within tissue to be imaged and relating to a given imaging modality may be received by a detector housed within imaging assembly 110, or may be received within imaging assembly and coupled to an external detector through an imaging energy guiding device within imaging conduit 120. Imaging couplers and related energy guiding devices may support one or more imaging modalities. For example, a fiber optic and lens or mirror assembly may be employed for the delivery of imaging energy related to both OCT and IR imaging modalities. Imaging energy associated with two or more imaging modalities may be produced and/or received by a common energy producing and/or receiving apparatus and mutually multiplexed in frequency or interleaved in time. Imaging probe 105 may be rotatable or may contain a rotating imaging element for achieving a radial field of view within a lumen.

In embodiments in which at least one imaging modality is optical imaging, the imaging assembly 110 typically contains the distal tip of a fiber optic, as well as a combination of optional optical components such as a lens (such as a ball lens or gradient refractive index lens, also known as a GRIN lens), which collectively serve the purpose of acting as an optical receiver, (a collection element for collecting optical energy from the tissue to be imaged) and may also serve as an optical emitter (a focusing and/or beam directing element for focusing and/or directing an emitted optical beam into the tissue to be imaged). A mirror and/or a prism are often incorporated as part of an optical emitter and/or receiver. The imaging assembly 110, connector 125 and/or imaging conduit 120 may be immersed in fluid, such as saline. For multimodal optical and acoustic imaging, imaging probe 105 may be compartmentalized such that there is at least one gas-filled compartment or lumen for optical imaging and at least one fluid-filled compartment or chamber for acoustic imaging.

The imaging conduit 120 typically includes at least one optical waveguide or at least one conductive wire (optionally two or more) that connects an emitter and/or receiver via connector 125 to adapter unit 140. Imaging conduit 120 may also act as a mechanical force transmission mechanism for rotating or translating the imaging assembly. For example, imaging conduit 120 may include a fiber optic, wrapped by two layers of electrical wire that are insulated from each other. Imaging conduit 120 may be further reinforced by other structural features, such as helically wrapped wires or other designs used to construct imaging torque cables for rotating scan mechanisms, as described known to those skilled in the art. Imaging conduit may also supply power to a micro-motor located in the distal end of imaging probe 105 for locally rotating one or more components of imaging assembly 110.

FIG. 3 provides a perspective drawing of an example embodiment of a multimodal imaging probe that may be employed as a component of a multimodal imaging system according to embodiments of the disclosure. The probe shown in FIG. 3 was disclosed in U.S. patent application Ser. No. 10/010,206, titled "Scanning Mechanisms for Imaging Probe" filed on Jan. 22, 2008, and U.S. patent application Ser. No. 12/385,014, titled "Scanning Mechanisms for Imaging Probe" and filed on Mar. 27, 2009, the contents of which are incorporated herein by reference in their entirety. Briefly, the imaging probe may include an imaging assembly, where the imaging assembly includes a movable member that is capable of directing in imaging energy beam at one or more angles in a forward-looking direction. In two non-limiting example implementations, the orientation of the movable member may be varied by changing the rotational velocity of the imaging assembly upon which the movable member is pivotable, or using a magnetic force or actuation means.

The example imaging probe incorporates both ultrasound (e.g. IVUS) and optical (e.g. OCT) modalities into a single catheter assembly for multimodal imaging. The system includes a flexible catheter containing a fiber optic 40 and a co-axial electrical wire 50. The proximal connector contains fiber optic 40 that can be received by the adapter to optically couple the imaging fiber optic 40 to the optical imaging system "back-end". There are also electrical connectors 56 that allow the one or more electrical conduits to be connected to the electronic or power circuitry and/or controller and processing units, such as those for an ultrasound processing system.

The imaging conduit of the present example rotates around its longitudinal axis, and the coupling of a rotating fiber optic probe can be accomplished using a fiber optic rotary joint incorporated either as part of the proximal connector of the imaging probe 10 or as part of the adapter 14. Similarly, conductive wires that rotate with the imaging conduit are coupled with relatively stationary conductors of the ultrasound circuitry and/or controller and processing units, for example, by means of slip rings or rotary transformers. These slip rings can be incorporated as part of the proximal connector of the imaging probe 10 or as part of the adapter 14.

FIG. 3(*a*) shows a cross sectional view of the midsection of the imaging probe of FIG. 3 taken along the dotted line which shows a fiber optic 40, guide wire port 44 and guide wire 42, imaging conduit 34, imaging conduit lumen 46, external sheath 48 which is a hollow, flexible elongate shaft made of a physiologically compatible material and having a diameter suitable to permit insertion of the hollow elongate shaft into bodily lumens and cavities, and coaxial electrical wiring 50.

The imaging probe may contain ports at one or more points along its length to facilitate flushing. The expanded detailed view of the end of the imaging probe 10 shown in FIG. 3(*b*) shows the distal end of the guidewire 42 extended beyond the end of the outer sheath 48 and a flush port 54 at the end of the sheath 48.

As shown in FIG. 3, the proximal end of the imaging probe 10 includes a guide wire port 55 into which guide wire 42 is inserted and the connector assembly 36 which includes a flush port 58 and electrical contacts 56 along the connector body.

FIG. 3(*c*) shows a schematic of how the rotary and non-rotary components of the imaging probe can be coupled with an adapter to the rest of an imaging system. FIG. 3(*d*) schematically shows how the rotating components of the imaging probe can be coupled to the rotating components of an adapter. The rotating components of each can be electrically, optically and/or mechanically coupled using connectors and other configurations known in the art. Similarly, the non-rotating components of the imaging probe can be coupled to the non-rotating components of the adapter 14. The adapter 14 can include slip rings, rotary transformers, optical rotary joints and other such implements for electrically or optically coupling a rotary component to a non-rotary component and enable communication of necessary electrical and optical signals with the rest of the system.

Dual-fiber optical rotary joints are also available but considerably more complex. Electrical coupling between any conductor mounted onto a rotating component in the imaging probe 12 can be coupled to non-rotating conducting elements via metallic slip rings and springs, metallic slip rings and brushes or other commonly known methods of forming conductive contact between a stationary conductor and a rotary conductor.

While the electrical, optical and mechanical connections are shown separately in FIG. 3(*d*), it is possible to reduce the several connectors that must each be separately connected between the probe and adapter with fewer connectors by combining several connectors into combined connectors, as needed for a specific embodiment.

FIG. 4 provides an example of the internal structure of the distal end of the imaging probe that incorporates a multimodal imaging assembly. The assembly includes a tiltable component 70 for deflecting imaging energy that is emitted and/or received by one or more components that are not attached directly to the tiltable component 70. An ultrasound transducer 88 and optical emitter 92 are provided for directing imaging energy towards the tiltable component 70. The imaging energy is then deflected by an energy deflecting component mounted on the tiltable component 70. For ultrasound imaging, the energy deflecting component (the tiltable component 70) may include an acoustically reflective surface, such as a solid metal surface (e.g. stainless steel) or crystalline surface, such as quartz crystal or glass or a hard polymer.

For optical imaging, the energy deflecting component (tiltable component 70) may include an optically reflective surface such as a mirror surface made from polished metal, metallized polymer such as metallized biaxially oriented polyethylene terephthalate (Mylar), sputtered or electrochemically deposited metal, metal foil or other reflective components such as thin film reflectors. Metals commonly used to make mirrors include aluminum, silver, steel, gold or chrome.

An example embodiment of a distal end 29 of an imaging probe 31 is shown in FIG. 4(*a*), in which the distal end contains an imaging assembly 30 that includes a tiltable component 70 where the tiltable component is a disc mounted on pins 72 that enable the disc 70 to pivot about a pin.

The pins 72 define the tilting axis of the tiltable disc 70. When the imaging assembly 30 is at rest, the disc 70 will remain in an arbitrary starting position. In the example shown, this starting position is defined by a stop 80 that corresponds to a maximal imaging angle, where a restoring force providing by a torsion spring 76 is pushing the disc 70 towards the aforementioned stop 80. FIG. 4(*b*) shows a cross section along hashed vertical line 2(*c*)-2(*c*) of FIG. 4(*a*).

If the tiltable component 70 is tilted away from its preferred orientation by an external force, such as gravity, magnetic forces, electrostatic forces, friction with another moving part or fluid, compressive forces, cantilever forces, normal forces or any other source of incompletely opposed torque on the tiltable component 70 around the tilt axis, the tilt angle will increase.

One or more stops 80 and 82 may limit the range of the tilt angle of the tiltable component 70. For example, stop 80 may be a post or lip extending from the shell 84 of the imaging assembly 30 as a stop to prevent the tilting component 70 from further changing its tilt angle while it makes contact with the stop 80. Therefore, the stop can be used to limit the tilt angle from exceeding a maximum value determined by the position of the stop. Once the tilt angle hits this maximum, the normal force exerted by the stop 80 on the tiltable component 70 opposes the restoring mechanism. In many embodiments, this maximum tilt angle is the tilt angle that is achieved when the imaging assembly 30 is at rest and at low rotational speeds.

An additional or alternative stop 82 can be included to create a minimum tilt angle that the tiltable component 70 will achieve at rotational speeds in the upper end of the operating range. Indeed, there are many situations in which there is no significant benefit in allowing the tilt angle to reach zero, as will become apparent in the following descriptions of specific embodiments.

Imaging assembly 30 may include one or more mechanisms that tend to cause the tiltable component 70 to have its tilting angle increase. For the purposes of this disclosure, such a mechanism is referred to as a restoring mechanism. The torsion spring 76 (as shown in FIGS. 4(*a*) and 4(*c*)) or a compression spring can be used as a restoring mechanism, where one end of the spring 76 is mechanically in contact with or coupled to the tiltable component 70. The other end is mechanically coupled to another part of the imaging probe 31, such as the body of the imaging assembly.

As the imaging assembly 30 rotates, the disc 70 will want to align itself such that the normal of the planes defined by the faces of the disc 70 are substantially parallel with the longitudinal axis. As seen in FIG. 4(c), the other stop 82 shown (which corresponds to a minimum imaging angle) will prevent the disc 70 from reaching its preferred orientation at high rotational speeds of the imaging assembly. With a suitably configured imaging assembly, the stop 82 that corresponds to a minimum imaging angle can correspond to an angle of zero, providing imaging in a direction parallel to the longitudinal axis of the imaging probe.

Another example of a multimodal imaging assembly for use in a multimodal imaging system is provided in FIG. 5, as taught in U.S. patent application Ser. No. 12/010,208, titled "Imaging Probe with Combined Ultrasound and Optical Means of Imaging", filed on Jan. 22, 2008 by Courtney et al., which is incorporated herein by reference in its entirety. Referring to FIG. 5(a), an imaging assembly 550 is provided which is configured to allow imaging by acoustic and optical means in the same direction, so that an acoustic transducer that allows light energy to travel through a channel in the transducer is utilized. Essentially, assembly 550 uses an acoustic transducer 502 that is altered to have an optically transmissive channel made through its substrate. The acoustic transducer 502 can be any kind of ultrasound transducer known in the art, such as piezoelectric composition (e.g. PZT or PVDF, single crystal piezoelectric), a composite transducer or a capacitive micromachined ultrasonic transducer (cMUT).

Electrical conductors 500 are directed to the conducting layers 501 on either side of the transducer's acoustic substrate 502. A fiber optic 503 provides an optical conduit for enabling optical imaging. One or more matching layers can be added to the emission surfaces of the transducer, such as an epoxy layer (such as a silver or copper conductive epoxy layer which may functionally also serve as one or both of the electrodes that drives the transducer), or a polymer (such as parylene or PVDF).

Conductive layers 501 on either side of the piezoelectric material 502 are incorporated as required for applying a voltage to the piezoelectric. The opening 507 is coupled to an optical waveguide 503, either directly, or by means of one or more mirrors or prisms and one or more lenses (not shown). If any optical components are included within the opening, a dampening, insulating layer of a compliant material 506, such as silicon or polymer may separate the optical components from the acoustic substrate 502 to act as either an electrical insulator or to minimize the transmission of stresses that are generated by the acoustic substrate 502 to the optical components.

As shown in FIG. 5(b), the light from the fiber can be directed towards a mirror 404 (or prism) that causes the light from the fiber to be deflected through the optically transmissive channel 507.

Yet another non-limiting example of a multimodal imaging system is provided in FIG. 1 of US Patent Publication No. 2009/0299195, titled "Multimodal Catheter System and Method for Intravascular Analysis", and filed by Muller et al., of which only FIG. 1 is incorporated herein by reference. The system combines intravascular ultrasound, optical coherence tomography, and near infrared spectroscopy for the detection of multiple, different abnormalities in the arterial morphology during a single intravascular procedure.

The above examples illustrate multimodal imaging systems, which may be adapted according to embodiments of the present disclosure as described below. It is to be understood that the preceding examples were merely provided as a non-limiting examples, and that other multimodal imaging probes may also be used with embodiments of the present disclosure.

Referring again to FIG. 1, multimodal imaging system 100 is configured for the displacement of an intraluminal medium during a non-invasive procedure to support an imaging modality that benefits from the displacement of intraluminal medium during imaging. Such displacement may be provided and controlled by one of many devices and subsystems, including, but not limited to, subsystems for displacement of intraluminal medium through intraluminal flushing, and subsystems for displacement of intraluminal medium through controlled occlusion of the lumen, as taught in US Patent Publication No. 2009/0299195 and U.S. Pat. No. 7,758,499, titled "Method and Apparatus for Viewing Through Blood", which is incorporated herein by reference in its entirety.

In one embodiment, intraluminal flushing may be achieved by providing flushing liquid to the imaging probe 105 through an input port, whereby the flush liquid is dispensed into the lumen via output ports provided at one or more points along the length of imaging probe. Alternatively, flushing liquid may be provided via a conventional guide catheter that is able to introduce fluid into the lumen to be imaging. Alternatively, flushing liquid may be provided via a specialized flush catheter, for example, as disclosed in U.S. Pat. No. 7,625,366, titled "Flush Catheter with Flow Directing Sheath", which is incorporated herein by reference in its entirety. Flushing liquid, such as a saline solution, Ringer's lactate solution or contrast agent, may be provided manually, for example, using an external syringe. In some example embodiments, flushing may be performed via an auto-injector, pressure infuser bag, a peristaltic pump, a syringe or piston pump, a valved system, a gravity pressurized system, and the external application of pressure to medium using automated or manual application of pressure.

In one embodiment, medium displacement apparatus, shown generally at 135, provides and/or regulates or controls one or more medium displacement operations. As noted above, medium displacement apparatus 135 may be interfaced with imaging probe 105, or may be provided as a separate apparatus (such as a guide catheter or specialized flush catheter) for achieving medium displacement. In a non-limiting example, medium displacement apparatus 135 may include an external pump (not shown) that provides controlled volumes of flush solution (from a reservoir) to a region of interest. In another example, medium displacement apparatus 135 may include an inflatable balloon housed on or within imaging probe 110 for achieving medium displacement by controlled inflation that results in full or partial occlusion of the lumen.

In another embodiment, medium displacement apparatus 135 may further include an external manual switch that only enables or authorizes automated displacement operations when the switch is activated by a user or physician. Such a switch enables a supervisory mode of semi-automated medium displacement, requiring that a human operator is actively involved in monitoring any automated displacement operations. Non-limiting examples of suitable switches include a button or a foot pedal that must be continuously depressed for automated displacement (e.g. injection or inflation) to take place.

Referring again to FIG. 1, driver and adapter unit 140 includes interfaces for facilitating transmission of power and/or signals within any fibers and/or wires between imaging probe 105 and the appropriate control and/or processing subsystems. It may include a motor driver subsystem 145 for imparting rotation motion to rotary components of the imaging probe. Motor drivers may also power a pullback mechanism, push-forward mechanism or a reciprocating push-pull mechanism to facilitate longitudinal translation of imaging assembly 110. Such longitudinal translation of imaging assembly 110 may occur in conjunction with the longitudinal translation of an external shaft (not shown) that surrounds the image assembly 110 and imaging conduit 120, or may occur within a relatively stationary external shaft.

Additional sensor subsystems may be incorporated as components of the driver and adapter unit 140, such as a position sensing subsystem 150, for example to sense the angle of rotation of a rotary component within imaging probe 110 and/or the longitudinal position of imaging assembly 110. Imaging probe 110 may also include a memory component such as an EEPROM or other programmable memory device that includes information relating to imaging probe 110 such as, for example, identifying specifications of imaging probe 110 and/or calibration information. Additionally, driver and adapter unit 140 may further include amplifiers 160 to improve the transmission of electrical signals or power between imaging probe 110 and the rest of the system.

Driver and adapter unit 140 is interfaced with control unit 165. Control unit 165 includes first 170 and second 175 imaging modality controller subsystems to support the multimodal imaging devices (the system may further include additional imaging modalities and controllers in addition to the two shown), which may include, but are not limited to, any of the following imaging modalities: 1) ultrasound, 2) optical coherence tomography, 3) angioscopy, 4) infrared imaging, 5) near infrared imaging, 6) Raman spectroscopy-based imaging and 7) fluorescence imaging.

While the first and second imaging modality controllers are shown as separate subsystems, it is to be understood that they may be one and the same. For example, OCT and near infrared (NIR) spectroscopy data can conceivably be acquired via a common light source and signal acquisition system. Similarly, when the first and second modalities are both IVUS, with one modality being a lower frequency IVUS than the other, the hardware required to generate and acquire the two sets of IVUS data may be the same, with different operating parameters.

An optical modality controller may include any or all of the following components: interferometer components, one or more optical reference arms, optical multiplexors, optical demultiplexers, light sources, photodetectors, spectrometers, polarization filters, polarization controllers, timing circuitry, analog to digital converters and other components known to facilitate any of the optical imaging techniques described herein or incorporated herein by reference.

An ultrasound modality controller may include any or all of the following components: pulse generators, electronic filters, analog to digital converters, parallel processing arrays, envelope detection, amplifiers including time gain compensation amplifiers and other components known to facilitate any of the acoustic imaging techniques described herein or incorporated herein by reference. Control unit 165 may include one or more of the following non-limiting list of subsystems: a motor drive controller 180, position sensing control circuitry 190, timing circuitry, volumetric imaging processors, scan converters and others.

As shown in FIG. 1, medium displacement apparatus 135 may be operated and/or controlled independent of control unit 165. For example, medium displacement apparatus 135 may include a syringe or a manual pump. In another embodiment, shown in FIG. 2, control unit 165 may further includes medium displacement controller 185, which monitors medium displacement operations and may also automate or semi-automate medium displacement operations. In an alternate embodiment, medium displacement controller 185 may be directly interfaced with medium displacement apparatus 135. Medium displacement controller 185 may monitor information including, but not limited to, a volume of flush solution provided for a given medium displacement operation, a total of flush solution provided for multiple medium displacement operations for a given patient and/or minimally invasive procedure, a time duration during which a given medium displacement operation is carried out, a total time duration over which multiple medium displacement operations are carried out for a given patient and/or minimally invasive procedure, and control signals and/or commands communicated to a device or subsystem for achieving medium displacement.

Medium displacement controller 185 may provide input to a feedback loop employed during control of a sequence of imaging and displacement operations coordinated by processing unit 205, as further described below.

Control unit 165 may further include an optional cardiac sensor controller 195 for controlling optional cardiac sensors 200, such as electrode sensors to acquire electrocardiogram signals from the body of the patient being imaged. The electrocardiogram signals may be used to time the acquisition of imaging data in situations where cardiac motion may have an impact on image quality. The electrocardiogram may also serve as a trigger for when to begin an acquisition sequence, such as when to begin changing the speed of rotation of a motor in order to cause a desired scan pattern to take effect. For example, ECG-triggered initiation of an imaging sequence may enable images to be acquired during a particular phase of the cardiac cycle, such as systole or diastole. The electrocardiogram signals optionally serves as a trigger for varying the rate of injection or inflation of the medium displacement system to allow the system to account for the pulsatile nature or blood flow under observed physiological conditions.

Control unit 165 is interfaced with processing unit 205, which includes a processor 210 and memory and/or storage subsystem 215 connected by a bus, and performs multiple processing functions for coordinating various aspects of system operation. It is to be understood that although control unit 165 and processing unit 205 are shown as distinct subsystems, they may be provided in a composite computing system 220. Furthermore, some or all of the elements of control unit 165 may be performed by processing unit 205. Furthermore, processor 210 may include several processing elements, such as one or more CPUs, field programmable gate arrays, GPUs, ASICs, DSP chips and other processing elements known in the art. Processing unit 205 may also be interfaced with display and user interface 225 for either real time display or display of data at a time later than the time at which imaging data is acquired.

Imaging system 100 may further include data storage components (such as memory, hard drives, removable storage devices, readers and recorders for portable storage media such as CDs and DVDs), which may be interfaced with components of the processing unit and/or control unit.

In one embodiment, processing unit 205 is programmed to analyze images obtained using a first imaging modality, and to utilize the imaging results to automate the recording of images based on a second imaging modality that requires or benefits from an intraluminal medium displacement operation during image acquisition. The first imaging modality may be compatible with intraluminal medium, such that it does not require an intraluminal displacement operation to images with sufficient diagnostic sensitivity or clinical utility.

In an embodiment in which the intraluminal liquid is blood, the first imaging/detection modality may be selected from the non-limiting list including grayscale IVUS, radio-frequency IVUS (e.g. Virtual Histology™, integrated backscatter or iMap™), elastography, NIR spectroscopy, sono-luminescent imaging, microbubble enhanced IVUS, targeted microbubble enhanced IVUS, photo-acoustic imaging, fluorescence spectroscopy, biosensors such as ion-selective field effect transistors, and the second imaging modality may be selected from the non-limiting list including OCT, angioscopy, NIR spectroscopy, Raman spectroscopy, IVUS, radio-frequency IVUS, elastography, sono-luminescent imaging, microbubble enhanced IVUS, targeted microbubble enhanced IVUS, fluorescence spectroscopy, and photo-acoustic imaging. A second imaging modality that is optical in nature may utilize wavelengths from the ultraviolet, visible, NIR, and/or infrared portions of the electromagnetic spectrum.

In another embodiment, the first and second imaging modalities may be a single imaging modality, for which images may be initially obtained in the presence of an intraluminal medium, and where improved images may be subsequently obtained via a displacement operation.

Even though ultrasound has reasonable penetration through blood, the displacement of blood from the field of view of an ultrasound imaging probe can still improve the ability to identify the wall of a vessel or provide improved image contrast. Meanwhile, ultrasound has the ability to better penetrate through biological media such as blood and soft tissues and has a depth of penetration that typically extends several millimeters or centimeters beyond that of optical coherence tomography.

In one example embodiment, the first and second imaging modalities are both IVUS, but the first modality is IVUS having a lower frequency range than the second IVUS modality. Generally speaking, higher frequencies of ultrasound provide higher resolution than lower frequencies, but higher frequencies do not penetrate through blood as well. Therefore, it may be desirable to displace blood when imaging with higher frequencies of IVUS. There may be separate ultrasound transducers for the two IVUS imaging frequencies, or the ultrasound transducers may have a wide enough bandwidth to be able to support two or more imaging frequencies, where the imaging frequencies are dictated in part by the frequency of the pulses used by a pulser to excite the ultrasound transducer.

The ability to combine ultrasound with optical imaging methods, such as OCT or near infrared spectroscopy using a single imaging probe, provides advantages with respect to selecting the required resolution and depth of penetration. Furthermore, much of the information acquired by optical coherence tomography is complementary to that acquired by ultrasound and analysis or display of information acquired by both imaging methods would improve the ability to better understand the interrogated tissue, such as with respect to its composition.

It should be noted that while intravascular OCT is significantly impeded by the presence of blood, NIR spectroscopy is less affected and is able to assess plaque composition up to a distance of a few millimeters through blood. However, it will be less effective in larger vessels and aneurysmal segments of otherwise normal-caliber vessels.

Figure 6:
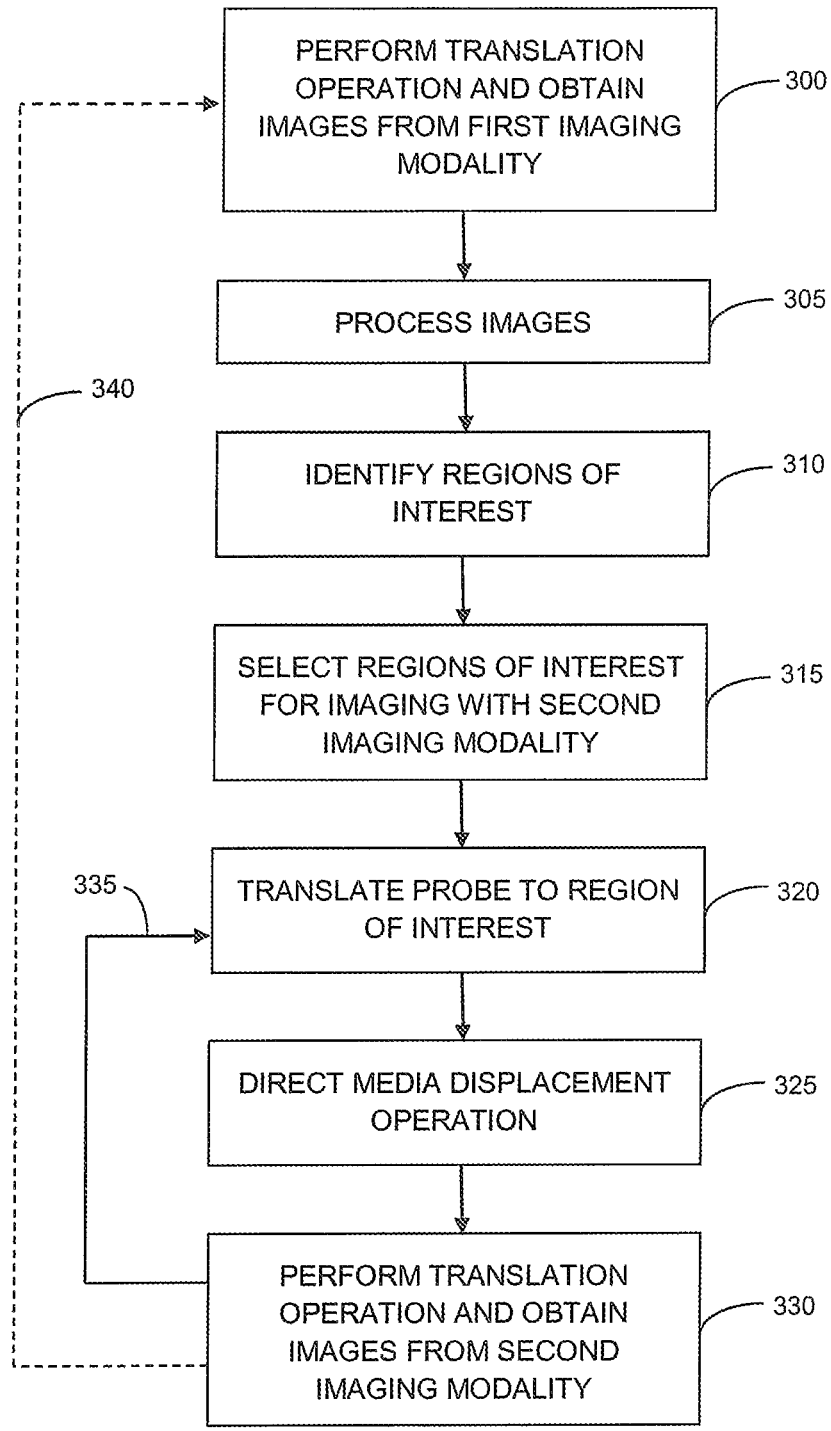
FIG. 6 is a flow chart describing a method of performing a minimally invasive procedure in which results obtained from a first imaging modality are employed to direct the acquisition of images using a second imaging modality that benefits from displacement of an intraluminal medium.

Referring to FIG. 6, a flow chart is provided that illustrates an embodiment in which images recorded using a first imaging modality are employed to direct a displacement operation when subsequently obtaining images from a second imaging modality, where the second imaging modality is impeded by the presence of a displaceable intraluminal medium.

In step 300, a multimodal imaging probe, such as imaging probe 105 in FIG. 1, is inserted into a lumen for obtaining images with a first imaging modality that is compatible with the presence of a displaceable intraluminal medium. A first imaging operation, which may be a translation operation such as a pullback, is performed while recording imaging data using the first imaging modality. The translation operation may be automated and performed at a constant translation rate that is selected and/or optimized for the first imaging modality. Signals obtained from the first imaging modality device (located in imaging assembly 110 of imaging probe 105) during the first translation operation are provided to first imaging modality controller 170.

According to the present embodiment, position sensing is employed during the translation operation to identify the location of the recorded images relative to a reference position and optionally a reference orientation. The recorded images are therefore correlated with the position, and optionally the orientation, of the imaging probe. Position sensing may be achieved using one of many known methods, and is generally represented in FIG. 1 by position sensor 150 and position sensing controller 190 (which may together form a composite subsystem).

In one embodiment, position sensing is obtained by intraluminal longitudinal position sensing, for example, using encoders or other position sensors connected to the imaging probe, pullback motor or drive element. Position sensing may be obtained via spatial domain measurements, or inferred based on time-domain measurements in which translational or rotary motion is performed at known rates. For example, position information relating to the longitudinal position of an imaging probe may be inferred based on a time interval over which translation occurs, provided that the rate of change of the position of the image probe is known during the time interval. The rate of change of position may be constant during probe translation. Angular orientation sensing may be obtained using rotary encoders or other position sensors connected to the imaging probe, as taught in co-pending U.S. patent application Ser. No. 12/010,207, titled "Medical Imaging Probe with Rotary Encoder" and filed on Jan. 22, 2008, which is incorporated herein by reference in its entirety.

In another embodiment, position sensing may be achieved using a sensing element located in the imaging probe that determines the location of the imaging probe in an externally created field, such as a magnetic field, which may be performed in combination with orientation sensing. A suitable sensor is provided by Mediguide Ltd., and may be employed as taught by Muller et al. in US Patent Application Publication No. 2009/0299195.

After having performed a first translation operation, image data from first imaging modality controller 170 is provided to processor 210 for image analysis in step 305. Processor 210 analyzes the image data according to an image processing algorithm to identify regions of interest, such as regions of diagnostic, research, and/or clinical interest. Regions identified may represent a wide range of anatomical structures and/or features, including, but not limited to, a desired tissue type for subsequent analysis, specific anatomical features, known or suspected pathological structures or features, and medical implants or other artificial structures. Suitable regions of interest include the following non-limiting list: plaque, possible thrombus, branch points, lesions, calcifications, implants such as stents or brachytherapy implants, stenoses, areas of vessel wall thickening, lipid cores, necrotic regions, fibrous caps, dissections, masses and the like. Regions of interest may further include regions with microbubbles detected, such as targeted microbubbles. They may also include regions of indeterminate or uncertain structure or composition, where an automated or semi-automated processing algorithm cannot confidently assess the region of interest without further imaging data.

Regions of interest may further include vascular lesions that have not led to clinical symptoms, but are at increased risk of rupturing or eroding and causing an acute myocardial infarction. These so-called "vulnerable plaques" are an area of interest as the prospect of treating such plaques to pre-empt adverse clinical events is conceptually appealing.

In another embodiment, a region of interest may be identified as any region where indeterminate results are suspected from any images obtained based on the first imaging modality. For example, when NIR spectroscopy is used as the first imaging modality, a region of interest may be defined for a region where the vessel wall is further from the imaging assembly with the imaging probe than allowed by the range of an NIR spectroscopy probe in the presence of blood. Alternatively, such a region may be defined for the case of IVUS imaging when the vessel wall is in contact with the imaging probe. IVUS can be subject to several artifacts in portions of the field of view closest to the catheter. These include a phenomenon known as transducer ring-down, as well as artifacts that arise from ultrasound reflections from the catheter sheath. OCT is substantially less affected by such artifacts and is capable of providing excellent images of portions of the field of view that are closest to the catheter.

In one embodiment, a region of interest may include a stent having a known geometrical shape, structural form and/or imaging signal characteristics. This could include metallic stents, polymeric stents, biodegradable stents, pacemaker wires, guidewires and the like.

Regions of interest may be identified using one of many known image analysis methods. Regions of interest may be identified by processing images to obtain metrics that can be compared with expected values or ranges. In another example implementation, image analysis is performed in combination with a pattern recognition method for identifying the regions of interest. In one example, the imaging analysis method includes border detection. For example, border detection may be employed for the detection of regions with plaque thickening that are suitable for subsequent imaging by the secondary imaging modality. Border detection may be achieved by a number of different methods. In one non-limiting example, border detection is described by Papadogiorgaki et al. using the contour optimization technique (Ultrasound in Medicine and Biology 2008, September 34(9) 1482-98). For example, methods of border detection are taught in U.S. Pat. No. 7,359,554, titled "System and Method for Identifying a Vascular Border" and US Patent Publication No. 2005/0249391, titled "Method for Segmentation of IVUS Image Sequences", both of which are incorporated herein by reference in their entirety.

In one embodiment, regions of interest are identified by image processing methods that involve tissue characterization techniques. For example, in applications in which the first imaging modality is IVUS or a variant thereof, regions of interest may be determined by the radio-frequency properties of the backscattered ultrasound signal combined with a pattern recognition algorithm, as taught by Nair in U.S. Pat. No. 6,200,268, which is incorporated herein by reference in its entirety. Tissue characterization techniques may alternatively employ analysis of the intensity of grayscale pixels. For example, certain intensity ranges of pixels in the generated images are more likely to represent soft plaque that may further include lipid-rich regions. Alternatively, texture analysis algorithms, such as wavelet decomposition algorithms or algorithms that assess statistical properties the imaging data may be used. Alternatively, heuristic algorithms that detect known properties of certain tissue components may be utilized. For example, an algorithm may detect acoustic shadowing, which is known to correlate well with the presence of calcifications in IVUS imaging.

It may be desirable to input several imaging data parameters into a pattern recognition algorithm that is able to identify the most likely tissue composition for a particular region. Such a pattern recognition algorithm could be a neural network, fuzzy logic algorithms, a data classification tree, nearest neighbor techniques, and several other pattern recognition techniques. Such a pattern recognition algorithm may be trained using imaging data for which the true underlying composition of the tissue is known, such as by any combination of histology, radiography, spectroscopy, ultrasound, optical imaging and others. Such a pattern recognition algorithm may identify not only the most likely underlying tissue composition for a given region of interest, but also provides an estimate of its likelihood of being correct. Alternatively, the pattern recognition algorithm can simply identify regions for which the underlying composition with the first imaging modality is uncertain, prompting the need for additional analysis with a second imaging modality.

Regions of interest may additionally or alternatively be determined based a non-imaging modality, such as based on temperature heterogeneity. An example method of detecting thermal heterogeneity is provided in Stefanidis C, et al., "Thermal heterogeneity within human atherosclerotic coronary arteries detected in vivo: a new method of detection by application of a special thermography catheter", Circulation 1999; 99; 1965-71. A temperature sensor may be incorporated into the distal region of probe 115 to detect a change in the temperature of the wall of the artery, where higher temperatures are thought to more likely correspond to inflammatory regions. In yet another embodiment, regions of interest may be defined based on regions having a minimum concentration of a locally detected biological analyte, such as markers of inflammation, for example detecting C-reactive protein (CRP) by a local biosensor such as an ion-selective field effect transistor (ISFET) having bound thereon a selective detection species such as an antibody or aptamer.

The aforementioned automated systems and methods for identifying regions of interest for further analysis by the second imaging modality may include settings that enable a user to adjust or vary the parameters that influence the identification of regions of interest. For example, such settings may enable the user to select specific pathological features or structures, such as the identification of regions having at least a selected amount of plaque, or a selected minimum vessel wall thickness, or a selected degree of eccentricity in the wall thickness. It is known that plaques are unlikely to reside in regions where there is minimal thickening of the vessel wall and that plaques tend to reside in regions where there is eccentric thickening of the vessel wall.

In another embodiment, the one or more threshold parameters that trigger the identification of a region of interest may be configurable. Such an embodiment is particularly important for applications in which contrast agent, saline solution, or another flush solution is dispensed during a medium displacement operation. By controlling the one or more threshold parameters for which a region of interest is identified, a clinician or operator may be able to control or limit the volume of flush solution delivered during a minimally invasive procedure to ensure that the volume of flush solution employed has a controlled or minimal impact on the patient.

Although the aforementioned embodiments involve automated methods of identifying a region of interest, it is further contemplated that regions of interest may be manually defined by a user or operator by reviewing the results of images obtained via the first translation (e.g. pullback) operation, and selecting regions of interest for a second automated or semi-automated secondary translation operation in which the regions of interest are imaged via the secondary imaging modality while performing medium displacement operations, as further described below.

A region of interest may also be defined or identified according to more than a single imaging modality. For example, the imaging probe may include multiple imaging modalities that are compatible with the presence of an intraluminal medium, and the region of interest may be identified by processing the multiple imaging modalities according to the methods described above.

Referring again to FIG. 6, after having obtained one or more regions of interest in step 305, regions of interest to be imaged during a second pullback operation with the second imaging modality are selected in step 310. This step may include automatically selecting all regions of interest identified in step 305, or alternatively, this step may include selecting a subset of the regions of interest identified in step 310. In the latter case, the selection of the subset of regions of interest may be performed by a user operating the system via user interface 225, or may be achieved by pre-selecting types of identified regions that are desired for subsequent analysis.

For example, although regions of interest may be identified in step 305 that relate to a wide range of normal anatomical structures, implants, tissue types, and pathological structures or signatures, the system may be configured to only image a detected implant using the second imaging modality. Alternatively, the system may rank the regions of interest identified in step 305 according to any of several criteria, such as, but not limited to, plaque size, predicted likelihood of being a thin-capped fibroatheroma, location in the vasculature and others. Once the regions of interest are ranked, a subset may be selected, such as a group of the regions of interest that ranked highest according to the criteria used.

Having selected the regions of interest for imaging via the second imaging modality (either automatically or via user intervention), a second pullback operation is then performed to image the selected regions of interest. This operation may be performed according to a number of embodiments, as further disclosed below.

Initially, the imaging probe (and/or a functional component thereof) is translated to a region of interest selected in step 315. The translation may be performed manually, with feedback from the position sensing system to determine when the probe has been moved to the appropriate location, and may additionally or alternatively involve the automated translation of the imaging probe to position the imaging assembly in the required location.

Image comparison techniques may assist or guide the automated translation of the imaging probe to the desired position. Cross-correlation techniques can be used to identify images or regions within an imaging dataset that are similar to each other. In its simplest form for a 2D image, this involves multiplying the intensity of each pixel in one image with the intensity of the corresponding pixel in another image, and calculating the sum of these products. A highly similar image will have a high sum of products. By repeatedly shifting, rotating and/or morphing one of the images with respect to the other and repeating the cross-correlation calculation, an assessment for the similarity of the two images can be made that takes into account these transformations.

Cross-correlation techniques can be extended to 3D imaging datasets or alternatively be focused on localized regions within 2D imaging datasets. Cross-correlation techniques can be applied to 2D imaging datasets that are derived from 3D imaging data. For example, rather than applying cross-correlation to cross-sectional images, 2D longitudinal images generated by extracting data in any plane from a series of 2D cross-sectional images that are stacked together to form a 3D dataset can be used. In the present embodiments, cross-correlation of a pre-selected image or imaging dataset corresponding to a start or stop point identified on a first pullback can be applied to imaging data being acquired during a second pullback to better identify the start or stop points for media displacements operations.

Prior to obtaining images via the second imaging modality, a displacement operation is initiated in step 325 for displacing the displaceable medium within the lumen, to support imaging via the second imaging modality. As described above, any suitable displacement operation may be performed, including, but not limited to, flushing or inflation. The displacement operation may be initiated prior to the completion of the translation step 320 such that the system anticipates the time at which a selected region of interest will be assessable by the second imaging modality, and that the displacement operation has had the desired effect of adequately displacing the intraluminal media by the time the translation step 320 results in the imaging probe being positioned properly for the second imaging modality to assess the selected region of interest with minimal or no time delay. While displacing the medium, a pullback operation is performed in step 330 for imaging the region of interest using the second imaging modality.

In one embodiment, when performing step 330, in which a translation operation is performed to obtain images from the second imaging modality, additional images may be obtained from the first modality to accommodate or correct for positional errors or disturbances, such as tissue motion and/or errors in position detecting system. If the imaging modalities are accurately co-registered, acquiring images concurrently with the first and second modality will provide images at the same location, without introducing errors from tissue motion (i.e. cardiac, respiratory, etc). In one embodiment, the displacement operation, pullback operation, and imaging operations are automated by the imaging system to image the selected region of interest. The displacement operation may be performed continuously during the second pullback operation, or may be performed over discrete time or distance intervals. The automated dispensing operation may be activated or enabled by a user during steps 325 and 330, for example, by continuously activating a switch such as a button or foot pedal. Such a supervisory mode of imaging automation assists in ensuring that all medium displacement operations are performed in the presence of an operator. The operator may interrupt the process, for example, if it is deemed that a volume of flush solution employed has exceeded a pre-selected amount.

In alternative embodiments, one or more of steps 330 and 335 may be manually performed. In one embodiment, both steps 330 and 335 are manually performed, and the positions at which to perform the displacement operation and imaging operations are suggested to a user based on the selected regions identified in step 315. For example, an operator may translate the imaging probe, and the system (for example, via user interface 225) may indicate to the user positions at which displacement and imaging are to be performed. The user may then manually perform a displacement operation using a manually actuated medium displacement apparatus 135 as shown in FIG. 1.

Figure 2:
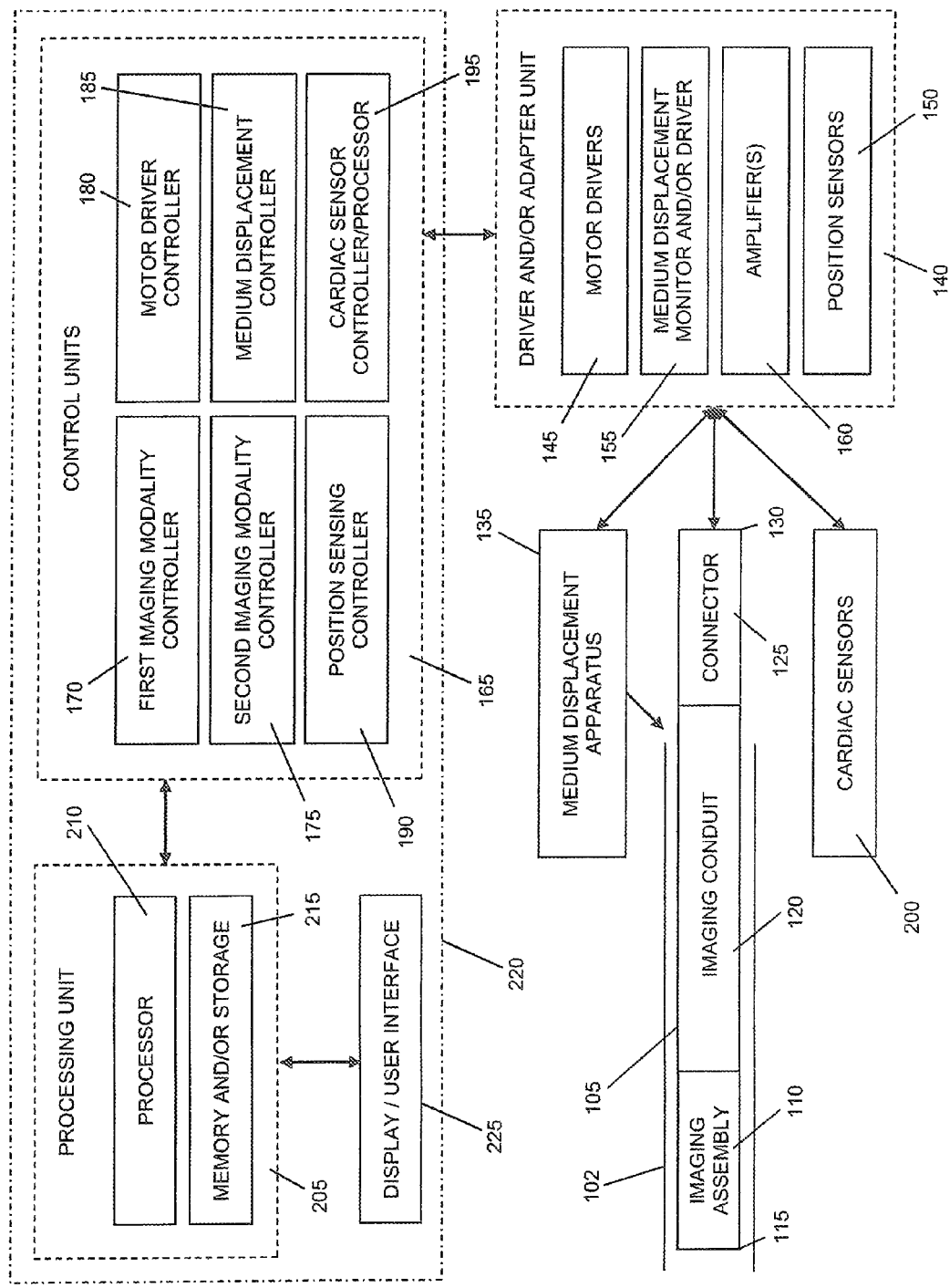
FIG. 2 is a block diagram illustrating a second system for performing multimodal imaging incorporating an integrated medium displacement system.

In another embodiment, the operator may manually translate the imaging probe, and the imaging system may perform automated dispensing and imaging when the imaging probe passes the regions of interest selected in step 315 (for example, using the integrated medium displacement apparatus 135 in FIG. 2, and related monitor/driver and controller components of the system.

In yet another example implementation, the imaging probe may be translated in an automated fashion, and the imaging system may indicate to the operator the locations at which a displacement operation is required for obtaining images via the second imaging modality. In such an embodiment, the system may automate the acquisition of images using the second imaging modality whenever a displacement operation is manually performed by the operator.

In one embodiment, the displacement operation is monitored, for example, by medium displacement monitor 155 shown in FIG. 2. As noted above, the parameters monitored may include a volume of flush solution provided for a given medium displacement operation, a total of flush solution provided for multiple medium displacement operations for a given patient and/or minimally invasive procedure, a time duration during which a given medium displacement operation is carried out, a total time duration over which multiple medium displacement operations are carried out for a given patient and/or minimally invasive procedure, and control signals and/or commands communicated to a device or subsystem for achieving medium displacement.

In one embodiment, a monitored displacement parameter is employed to provide feedback to the imaging system. The system may be provided with threshold ranges or maximum values for monitored displacement parameters. Exceeding such threshold values may trigger a visible or audible alarm. Alternatively, exceeding a threshold may result in automatic suspension or termination of a given displacement operation (and optionally alerting an operator of the event). Monitored displacement parameters may be stored and made available to an operator or clinician following a minimally invasive procedure, for example, to be included in documentation relating to the procedure. Alternatively, monitoring of a displacement operation may be employed to determine a time interval or a distance interval over which to perform steps 325 and 330. For example, after translating the imaging probe to a region of interest in step 320 and initiating a displacement operation in step 325, the imaging probe may be further translated while imaging and displacing the intraluminal medium until a monitored displacement threshold is exceeded.

It may be desirable to utilize feedback from the processed images in the above embodiments to control and/or optimize the rate of translation and/or rotation of the imaging probe. The pullback or push-forward speed, and/or the rotational speed of a torque cable may be controlled by the processing unit 205 and/or the controller unit 165. These speeds may be modified, determined and/or optimized separately for each imaging modality. Additionally, the speeds may be modified based on images processed by processing unit 205. For example, when assessing the images obtained by the first imaging modality, if the first imaging modality detects a region where the second imaging modality is to be activated, it may be desirable to increase the speed of pullback and/or the speed of rotation of the torque cable while the second imaging modality (for example, OCT) is being used. Speeding up image acquisition during operation of an imaging modality that requires displacement of intraluminal media may help reduce the duration of displacement or the amount of displacing media, such as contrast, that would need to be introduced while images are obtained.

In one embodiment, it may be desirable to selectively disable one or more of the imaging modalities as the speed of rotation or the speed of translation are adjusted. For example, a first modality may identify a region of interest that initiates a media displacement operation, activates a second imaging modality, changes the speed of rotation and/or changes the speed of pullback. If the first modality is rendered less useful by operation at a different speed of rotation and/or speed of pullback, it may be desirable to temporarily disable the first modality until a controller determines that the second modality is to be deactivated.

For example, if IVUS is the first imaging modality, the system may operate at a rotational speed in the range of 5 to 100 frames per second during IVUS analysis, in which IVUS identifies a region of interest. However, while imaging with a second imaging modality, such as OCT, the rotational speed may be increased to greater than 50 frames per second and the pullback speed may be increased to greater than 2 mm/s. While the limits of rotational speed for useful IVUS image acquisition are implementation specific and application specific, it is recognized that it may be reasonable to either disable or discard IVUS images during OCT acquisitions that employ rapid rotational speeds. In such a case, the end of the region of interest can be identified by the second imaging modality or any of several previously mentioned parameters that do not rely on the first imaging modality to identify the endpoint of a region of interest, such as time expired, volume of displacement media used or reaching a known position based on position sensor data from the pullback mechanism.

In yet another embodiment, during steps 325 and 330, image processing of the images obtained using the second imaging modality may be performed in real-time to assess the quality of the images. For example, image quality may be assessed by comparing the intensity, signal attenuation or texture of sections of the image, such as sectors, to pre-set desired ranges or thresholds. The images may be analyzed, for example, by the processing unit 205, to ensure that the border of the anatomic structure is relatively or sufficiently contiguous (for example, as defined by a pre-selected metric), with a well delineated border between the vessel wall and the lumen, as would be expected with adequate flushing.

Alternatively, sections of the image can be analyzed to detect or infer the presence of an intraluminal medium such as blood. Blood will typically have a signature or range of appearances for each modality, whether it be based on signal intensity, signal attenuation or, in the case of NIR imaging, spectral content. The quality of the image can be ascertained, at least in part, by ensuring that the signature of blood is not present in each section of the image from which it is desired to have blood displaced.

The perceived image quality may then be employed to provide feedback to step 325 and regulate the medium displacement operation. For example, if an image is deemed to be characterized by a poor signal-to-noise ratio, the rate of delivery of flush solution, volume of flush solution, time profile of amount flushed, or the volume of inflation for a displacement balloon, may be varied.

Alternatively, data from a non-invasive imaging modality may be used to assess the adequacy of displacement of intraluminal media. For example, an angiogram can be processed in real time or shortly after the displacement means is activated and the resulting images can be processed to determine if the vessel is fully opacified by contrast media. This determination can be done by assessing the change in pixel intensities of the angiogram or by assessing the sharpness of vessel borders in the angiogram.

In one embodiment, the image quality obtained by the second imaging modality is assessed in real time, and feedback provided to regulate a parameter related to the displacement operation in order to minimize aspects of the displacement operation. The image quality may be assessed to minimize the time of a displacement operation, the rate of delivery of a flush solution, and/or the volume of flush solution.

In another embodiment, the second pullback operation in step 330 may be initiated once the field of view is adequately improved with flushing based on real time image analysis, after which the imaging probe continues to translate for the acquisition of images until the end of the region of interest. If, in that time period, the field of view provides inadequate image quality, the pullback controller may stop and/or stepback, and resume translation once the field of view is adequate based on the assessment of image quality.

After having performed step 330 and obtained images of a given region of interest using the second imaging modality, the steps 320 to 330 may be repeated as indicated at 335 to obtain images of additional regions of interest selected in step 315. Accordingly, the method may be performed by performing a full pullback operation in step 300 to identify and select regions of interest, followed by serial pullback and displacement operations in steps 320 to 330 to acquire images for the selected regions of interest using the second imaging modality.

In an alternative embodiment, the initial pullback operation 300 may performed as a partial pullback operation, in which the pullback operation spans only a portion of the total anatomical region to be imaged. Image analysis step 305 may be performed in real time to identify regions of interest "on the fly". Such regions of interest may then be displayed to a user for real-time selection and subsequent automation of the second pullback, displacement and imaging operations in steps 320-300, for example, in a push-pull reciprocal fashion. Alternatively, the regions of interest may be automatically selected for subsequent analysis, as described above, and steps 320-330 are automatically performed. After having performed steps 300-330 based on a partial pullback operation, additional partial pullback operations are repeated, as shown at 340, until the minimally invasive procedure is deemed complete.

In one embodiment, image processing is employed to assist in identifying the start and stop points of a region of interest during a secondary pullback operation. In general, there may be some inaccuracy in the ability to accurately determine a relative position of the imaging probe for secondary pullback operations using many of the position-sensors due to slack in the imaging conduit, cardiac motion, flow and potential inadvertent movement of the catheters by the user.

In one embodiment, the positioning system is used as a first estimate of when to start and/or stop a secondary pullback operation, and one or more original images taken near the start/stop points from the first pullback operation are employed to compare against the current images acquired during the second pullback operation until an adequate match is found and the beginning of a region of interest is accurately identified. In addition to pathological regions of interest, such relative positioning may be improved using normal anatomical landmarks, such as bifurcations of the vascular anatomy.

Image comparison for determining the accurate starting position of a region of interest during a secondary imaging operation may be achieved by one of several known image comparison methods. In one embodiment, image cross-correlation is employed. In another embodiment, the size of the vessel lumen is employed. In yet another embodiment, the shape of the vessel border (between the media and adventitia layers) is employed. In yet another embodiment, the shape of the lumen border is employed. In yet another embodiment, the presence, shape or size of one more features detected by the first imaging modality, such as calcifications, bifurcations, implants, plaque, thrombus etc are employed. In one embodiment, a combination of position sensor information, image comparison techniques and/or geometric features of the regions are employed to help identify the start and/or stop points.

Figure 7:
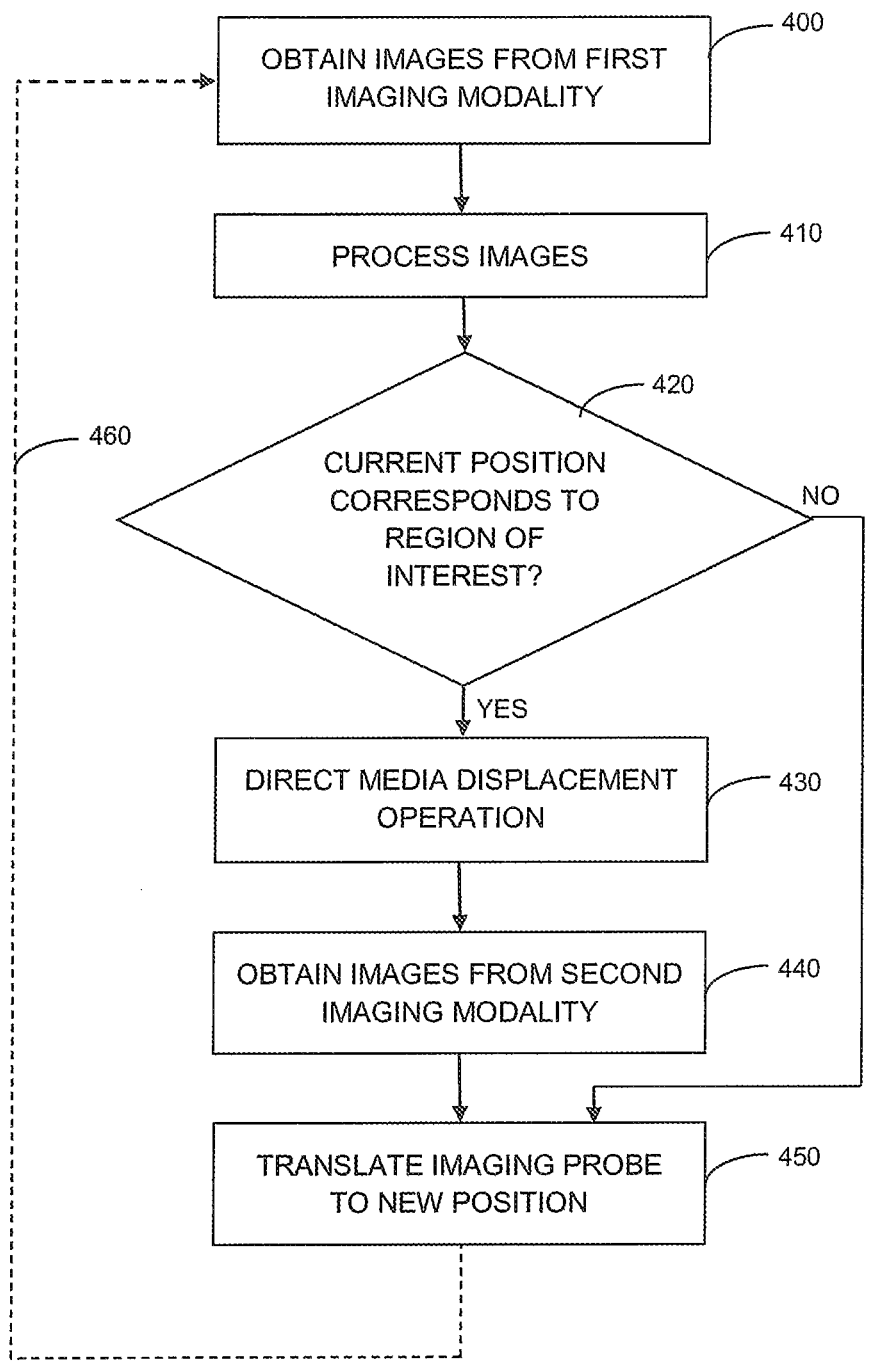
FIG. 7 is a flow chart describing a method of performing a minimally invasive procedure in which results obtained from a first imaging modality are employed in real time to direct the acquisition of images using a second imaging modality that benefits from displacement of an intraluminal medium.

In one embodiment, the real-time processing of images is performed to support real-time displacement and imaging by the second imaging modality without requiring a second pullback operation. This real-time embodiment is illustrated in the flow chart provided in FIG. 7. In step 400, after having positioned the imaging probe at an initial location, one or more images are obtained using the first imaging modality. The images are processed in step 410 according to methods described in the above embodiments. The real-time image processing may involve processing of individual images on an isolated basis to determine whether or not an image corresponding to the current location of the imaging probe is of interest for secondary imaging, or determining whether or not the current position corresponds to a region of interest based on an aggregated analysis of images in a spatial region preceding the present position. Alternatively, the real-time image processing may involve processing of a sequence of images that would correspond to a 3D dataset to provide greater certainty as to the presence of a region of potential interest for imaging with the second modality.

In step 420, a decision is made as to whether or not the current position corresponds to a region of interest. If the results from the image processing step suggest that the current position corresponds to a region of interest, then step 430 is performed, and a media displacement operation is directed. In another example, the decision may also be based on information from a fiducial marker (such as, but not limited to, a marker band detectable via angiography). As noted above, this may be performed either in an automated fashion, or in a semi-automated fashion in which the system prompts the operator to perform or activate the medium displacement operation. After the medium displacement operation is initiated, the secondary imaging modality is employed in step 440 to obtain images at the current position. The imaging probe is then translated to a new position in step 450, and the process is repeated according to step 460.

If, however, in step 420, the current position is not deemed to correspond to a region of interest, steps 430 and 440 are bypassed, and step 450 is executed by translating the imaging probe to a new position. The process is then repeated according to step 460. The aforementioned real-time method is either performed in a stop-start manner, as disclosed, where the imaging probe is at rest when medium displacement and secondary imaging steps are performed, or with continuous pull-back.

Although the preceding embodiment was illustrated as a series of discrete steps, it is to be understood that other variations of the embodiment may implemented. For example, in a variation of the above embodiment, the imaging probe may be translated using a motor or other drive system that is not immediately stopped while the image processing step is performed, such that by the time that the determination is made that a region of interest has been identified, the probe (or functional component of the probe) may have been translated slightly beyond the position at which the images were obtained. In one example, this may be remedied by translating the functional component of the image probe in backwards direction by a suitable amount prior to initiating the displacement operation. Alternatively, if the overshoot is sufficiently small, the displacement operation may be directly initiated without a corrective backward translation step. In other embodiments, the imaging probe may be translated continuously while performing one or more of steps 400 to 430 of FIG. 7.

In one embodiment, where continuous pullback is employed, the controller for the secondary imaging modality can identify when suboptimal imaging data has been acquired and declare (for example, via a notification) that a fault has occurred. The fault may be responded to by reversing the direction of translation of the imaging probe until the region that corresponded to the fault has been traversed, and re-initiating steps 430 to 450 while resuming the normal direction of translation.

Alternatively, having initiated a medium displacement operation in step 430 based on identifying a particular position as a region of interest, the medium displacement operation may continue to be activated while repeating the process, until a new position is reached that is no longer identified as a region of interest. When such a new position is reached, the medium displacement operation is terminated after performing step 420, and before performing step 450. Such an embodiment enables the automation of a serial measurement cycle in which secondary imaging is performed at multiple successive positions without having to terminate and re-initiate a medium displacement operation.

In a variation of the above approach, it may be preferable to translate the imaging probe in a reverse direction over a small distance prior to performing a medium displacement operation. Alternatively, a small reverse step (for example, on the order of <20 mm, and more preferably <5 mm) may be taken after automatically identifying the start of region of interest so that the leading edge of the region of interest is included with the imaging data collected after blood is displaced. For example, a pullback operation may be executed until a region of interest is identified, upon which a reverse (e.g. push-forward) step of approximately 2 mm is taken, followed by the initiation of a medium displacement operation. The pullback operation is then resumed for imaging with the secondary (and optionally the primary) imaging modalities, until end of a region of interest is identified, at which point the displacement operation is ceased. This method would then be repeated to identify and image the next region of interest.

An imaging probe for use with the aforementioned real-time embodiments may include a more proximal sensor for detection of regions of interest based on the first imaging modality (compatible with the intraluminal medium) and a more distal sensor based on a second imaging modality whose performance is improved via detection of regions of interest by the more proximal sensor and the displacement of the intraluminal medium.

More generally, an imaging probe for use with the aforementioned real-time embodiments may include a sensor positioned or oriented on the probe for detection of regions of interest based on the first imaging modality (compatible with the intraluminal medium) such that it will assess a potential region of interest before a second sensor based on a second imaging modality is positioned or oriented to assess the corresponding regions of interest, whose performance is improved via detection of regions of interest by the first sensor and the displacement of the intraluminal medium.

While some of the aforementioned embodiments employ a second pullback operation to obtain images using the second imaging modality in combination with a displacement operation, it is to be understood that the second imaging step may be executed by directing the probe in a forward direction as opposed to a reverse direction. In particular, such a push-forward operation may be favorable as the imaging assembly will be moving in the same direction as a bolus of displacing fluid, allowing more of a vessel to be imaged with a given amount of displacement fluid (because the imaging core follows the displacing fluid rather than travelling in an opposite direction of it). Furthermore, it is to be understood that a pullback operation may be achieved by pullback of the total imaging probe, or pullback of a core component of an imaging probe.

In another embodiment, the images obtained from the first and second imaging modalities may be processed to provide a score or index indicating how successfully a minimally invasive procedure involving combined imaging modalities was executed. For example, the score or index may be determined by calculating the percentage or absolute value of the pullback length where adequate displacement of intraluminal media took place. Such a score or index could be used to determine which datasets provide adequate quality for the purposes of a particular study or trial. Alternatively, the score or index could provide an indication as to whether or not a minimally invasive procedure should be repeated, possibly with varied parameters such as sensitivity and/or speed.

It is to be understood that while the aforementioned embodiments have recited methods and systems pertaining to multimodal imaging probes comprising two imaging modalities, the imaging probe may include additional imaging modalities. In one embodiment, multiple imaging modalities compatible with the presence of an intraluminal medium may be utilized for the identification of regions of interest. Additionally, multiple imaging modalities that benefit from the displacement of the displaceable intraluminal medium may be employed for the imaging of identified regions of interest.

In the preceding embodiments, emphasis has been placed on operations where the region or field of view assessed by one or more sensors is determined substantially by translation operations, such as pullback or push-forward operations. The methods and devices described apply equally to other imaging systems where the region imaged, assessed or treated by the first and second modalities is determined by operations other than a translation. For example, the imaging probe 31 described in FIGS. 4a to 4d is capable of imaging a broad region with both optical and ultrasound imaging and the imaging angle is determined in part by the tilt angle of deflectable component 70. For such a probe, the embodiments for controlling media displacement described above and in FIGS. 6 and 7 can have the translation operation substituted by a deflection operation. For example, when the imaging angle is large, ultrasound imaging may determine that there is no region of interest in the present field of view that requires further analysis with a second imaging modality. A region of interest may be identified at a more forward-looking imaging angle that would benefit from media displacement operations.

Similarly, electronic steering methods, such as those used with 2D or 3D ultrasound probes, such as linear array ultrasound transducers or phased array transducers, do not rely solely on translation or deflection to determine the region imaged. Such arrays may be incorporated into minimally invasive imaging probes and may be used as either the first or second or both of the imaging modalities for the present disclosure, and may benefit from the use of media displacement operations.

Figure 8:
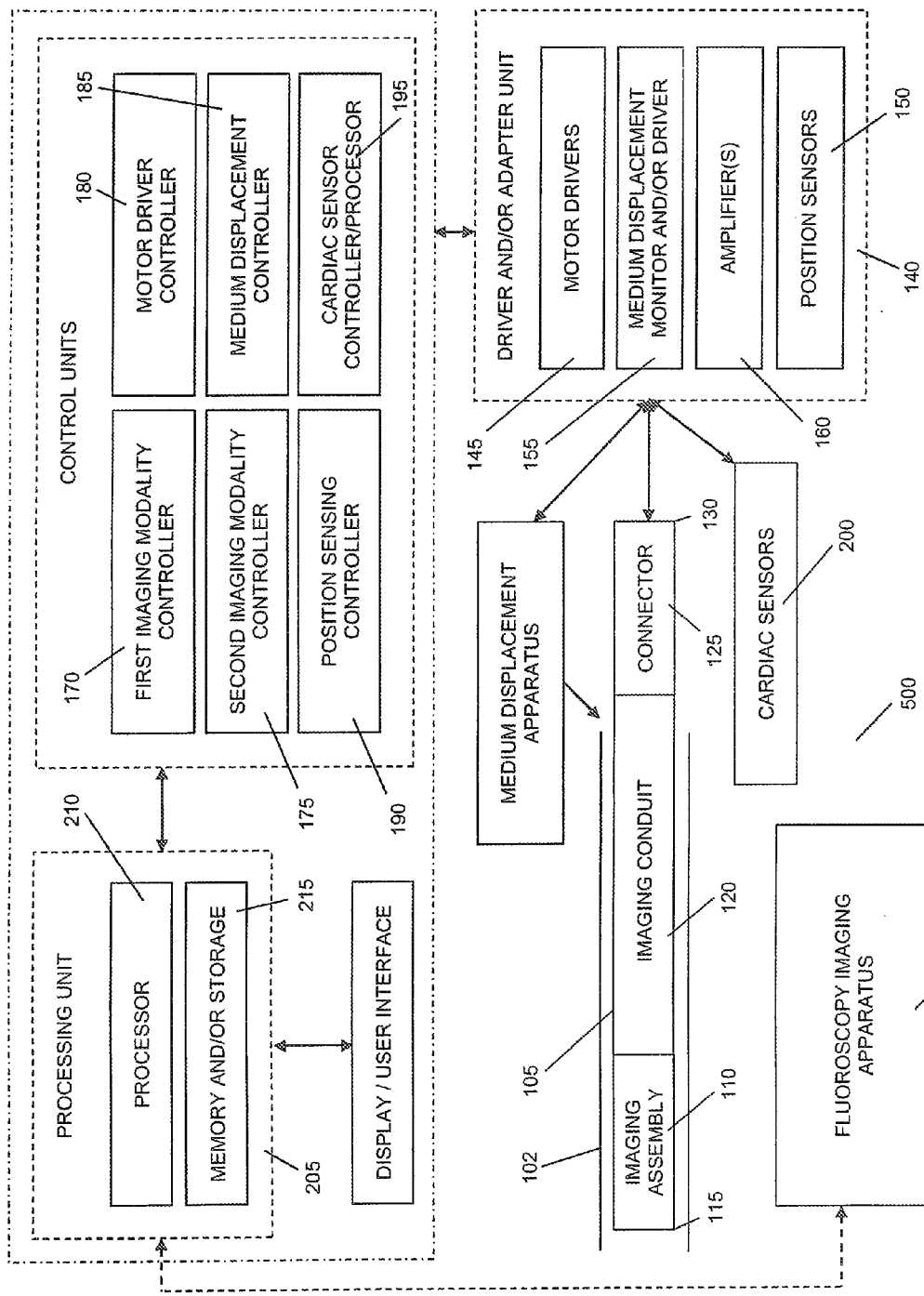
FIG. 8 is a block diagram illustrating a system for performing multimodal imaging incorporating an integrated medium displacement system and an external imaging apparatus.

In yet another embodiment, an external imaging apparatus may form a component of the system. Examples of external imaging modalities include angiography, CT angiography, magnetic resonance imaging and externally applied ultrasound. In one example embodiment, shown in FIG. 8, system 500 may include a fluoroscopy imaging apparatus 510 that is optionally connected to computing system 220 (for example, connected to processing unit 205). While performing a translation operation and collecting images via the first or second imaging modalities, an image acquisition trigger signal may be provided to the external imaging apparatus that triggers the external system to collect one or more frames of images during one or more translation operations of the imaging probe. In one example, the signal may be provided at intervals of interest, where such intervals may be, for example, uniformly separated in time or along the range of a translation operation. Alternatively, the intervals may occur at time intervals related to the initiation or termination of medium displacement operation or at points when the imaging probe is imaging a determined region of interest.

In another embodiment, the external imaging apparatus may be employed to identify one or more a regions of interest. The regions of interest may then be employed for subsequent imaging using an imaging modality of the imaging probe, wherein the imaging modality of the imaging probe benefits from the displacement of an intraluminal medium. In one example implementation, the first imaging modality is a fluoroscopy imaging device and the system is configured for the delivery of a contrast medium (for example, during an cardiac angiography procedure). During an initial operation, the fluoroscopy imaging device is employed to image a region including a lumen into which the imaging probe may be advanced.

In the case of fluoroscopy imaging, the imaging probe, or an additional flush catheter, may be initially employed to deliver contrast media within the lumen while acquiring one or more initial fluoroscopy images. The acquired initial fluoroscopy image or images may be employed to identify one or more regions of interest to be imaged by the imaging modality of the imaging probe. The one or more regions of interest may be manually identified by observation of the one or more initial images. For example, one or more of the regions of interest may correspond to locations of luminal narrowing.

In one example implementation, the external diagnostic apparatus may be employed to guide the imaging catheter to the region of interest identified on the one or more initial images. For example, the imaging probe may include a fiducial marker, such as a radiopaque marker (e.g. a radiopaque marker band), which enables the identification of the location of the imaging assembly using the external imaging apparatus. Accordingly, the imaging probe may be positioned such that it can be translated through a path that is known to contain one or more regions of interest using the external imaging apparatus, and the location of the imaging probe during a translation operation may be tracked using the external diagnostic apparatus and compared to the initial images to identify whether or not medium displacement is required at the current location.

In yet another example implementation involving an external diagnostic imaging device, the imaging probe may include first and second imaging modalities, where the first imaging modality is compatible with the presence of an intraluminal medium, and where the second imaging modality benefits from the displacement of the intraluminal medium. The regions of interest for acquiring images with the second imaging modality (while performing a medium displacement operation) may be identified by both the external diagnostic device (as described above) and the first imaging modality (during an initial translation and imaging operation involving the first imaging modality).

Generally speaking, it is to be understood that the intraluminal medium may be any medium that potentially impairs the performance of an imaging modality. Furthermore, while the above embodiments relate to intraluminal probe-based imaging methods involving the displacement of an intraluminal fluid, it is to be understood that the aforementioned methods may be applied to any medical imaging application in which a first imaging modality may be employed to direct the displacement of a displaceable medium for improving or supporting imaging based on a second imaging modality.

Suitable applications for the aforementioned embodiment of the disclosure involve imaging of the gastrointestinal system, the cardiovascular system (including coronary, peripheral and neurological vasculature), respiratory system, eyes (including the retina), auditory system, genitourinary systems, and many others.

Finally, it is to be understood that while the preceding embodiments have disclosed methods in which the process of obtaining images from a second imaging modality is aided by the medium displacement operation, it is to be understood that the use of a second imaging modality is but one example of a second minimally invasive procedure that is aided or improved by the medium displacement operation. Accordingly, on other embodiments, the aforementioned methods may be adapted to enable a minimally invasive procedure such as automated or semi-automated delivery of a therapy to a region of interest, where the therapy requires or benefits from a medium displacement operation. For example, in the aforementioned methods, the secondary imaging step may be combined with, or alternatively replaced by, a treatment operation that is performed over a region of interest while performing a medium displacement operation. Non-limiting examples of such therapeutic minimally invasive procedures include photodynamic therapy, laser ablation, and the application of electrical energy, such as radiofrequency energy, where the delivery of the treatment is guided by the regions of interest identified during a pullback operation involving a primary imaging modality that is compatible with the presence of the intraluminal medium.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of directing a medium displacement operation for performing a minimally invasive procedure within a lumen or cavity, the method comprising the steps of:
    obtaining a first set of images from a first imaging modality when a first translation operation of a functional component of an imaging probe is performed;
    spatially correlating the first set of images with an associated position of the functional component of the imaging probe, wherein the first imaging modality is compatible with a presence of a displaceable medium;
    processing the first set of images and identifying a region of interest; and
    directing a medium displacement operation while a second translation operation of the functional component of the imaging probe is performed over the region of interest;

wherein the minimally invasive procedure is performed within the region of interest during the medium displacement operation.

2. The method according to claim 1 wherein the minimally invasive procedure is improved by the medium displacement operation.

3. The method according to claim 1 wherein the imaging probe comprises an additional imaging modality compatible with a presence of the displaceable medium, the method further comprising the steps of:
obtaining an additional set of images from the additional imaging modality when the first translation operation is performed, and wherein the additional set of images are spatially correlated with the position of the functional component of the imaging probe; and
processing the additional set of images and further identifying the region of interest.

4. The method according to claim 1 wherein the minimally invasive procedure is a therapeutic procedure.

5. The method according to claim 1 further comprising the steps of:
processing the first set of images and identifying an additional region of interest;
directing an additional medium displacement operation while an additional translation operation is performed over the additional region of interest; and
wherein an additional minimally invasive operation is performed within the additional region of interest during the additional medium displacement operation.

6. The method according to claim 1 wherein one or more of the first translation operation and the second translation operation are manually performed.

7. The method according to claim 1 further comprising the steps of automating one or more of the first translation operation and the second translation operation.

8. The method according to claim 1 wherein the step of directing the medium displacement operation comprises indicating to an operator that the medium displacement operation is to be performed when the imaging probe is translated within the region of interest.

9. The method according to claim 1 wherein the step of directing the medium displacement operation comprises automating the medium displacement operation.

10. The method according to claim 9 wherein the medium displacement operation is automated after receiving an input from a user authorizing the medium displacement operation.

11. The method according to claim 9 wherein the step of automating the medium displacement operation comprises controlling a medium displacement apparatus to perform the medium displacement operation.

12. The method according to claim 11 wherein the medium displacement apparatus includes a fluid delivery apparatus.

13. The method according to claim 12 wherein the fluid delivery apparatus further comprises a component selected from the group consisting of an auto-injector, pressure infuser bag, peristaltic pump, syringe pump, piston pump, valved system, gravity pressurized system, and a means for the external application of pressure.

14. The method according to claim 1 further comprising the step of monitoring a parameter related to the medium displacement operation.

15. The method according to claim 14 further comprising the steps of alerting an operator or terminating the medium displacement operation when the parameter does not lie within a pre-determined range of values.

16. The method according to claim 1 wherein the step of processing the first set of images comprises processing three-dimensional image data.

17. The method according to claim 1 wherein the step of identifying the region of interest comprises comparing the first set of images to known or expected properties.

18. The method according to claim 17 wherein the known or expected properties are spatial profiles and/or tissue types of one or more of normal anatomical features, pathological anatomical features, and medical implants.

19. The method according to claim 17 wherein the step of comparing the first set of images to known or expected properties comprises computing a comparison metric and comparing the comparison metric with a threshold value or range of values.

20. The method according to claim 19 wherein the threshold value is configurable by an operator.

21. The method according to claim 1 wherein more than one region of interest is identified, the method further comprising the steps of:
ranking the regions of interest according to predetermined criteria; and
selecting a subset of the regions of interest according to the ranking;
wherein the steps of directing the medium displacement operation while the second translation operation is performed over the region of interest are performed for each region of interest within the subset.

22. The method according to claim 1 wherein the step of processing the first set of images includes executing a pattern recognition algorithm.

23. The method according to claim 1 wherein the step of processing the first set of images includes one of determining a spatial profile of a detected border, a tissue type, and a temperature profile.

24. The method according to claim 23 wherein the first imaging modality is intravascular ultrasound, and wherein the step of determining a tissue type comprises analysis of radio-frequency properties of a backscattered ultrasound signal.

25. The method according to claim 23 wherein the step of determining a tissue type comprises performing a method selected from the group consisting of grayscale pixel analysis, radiofrequency analysis, texture analysis, and heuristic analysis.

26. The method according to claim 1 wherein the region of interest includes a substance or feature selected from the group consisting of plaque, thrombus, branch points, lesions, calcifications, stents, brachytherapy implants, stenoses, areas of vessel wall thickening, lipid cores, necrotic regions, fibrous caps, dissections, microbubbles, targeted microbubbles, vascular lesions, and a combination thereof.

27. The method according to claim 1 wherein the region of interest is associated with indeterminate results obtained by processing the first set of images.

28. The method according to claim 1 wherein the step of identifying the region of interest includes the steps of:
providing the first set of images to an operator; and
receiving input from the operator, wherein the input identifies the region of interest.

29. The method according to claim 28 wherein the input comprises a subset of images, the subset corresponding to the region of interest, and wherein the step of identifying the region of interest further comprises identifying a relative position range corresponding to the subset of the first set of images.

30. The method according to claim 28 wherein the step of providing the first set of images to the operator further comprises providing a relative position corresponding to each image within the first set of images, wherein the input comprises a relative position range corresponding to a subset of the first set of images.

31. The method according to claim 1 wherein the first imaging modality is selected from the group consisting of grayscale IVUS, radio-frequency IVUS, Virtual Histology™, integrated backscatter, iMap™ elastography, NIR spectroscopy, sono-luminescent imaging, microbubble enhanced IVUS, targeted microbubble enhanced IVUS, photo-acoustic imaging, fluorescence spectroscopy, biosensors, and ion-selective field effect transistors.

32. The method according to claim 1 wherein the minimally invasive procedure includes the steps of obtaining a second set of images obtained from a second imaging modality while the medium displacement operation is performed, and spatially correlating the second set of images with an associated position of the functional component of the imaging probe.

33. The method according to claim 32 further comprising processing the first set of images and the second set of images to spatially correlate the first set of images with the second set of images.

34. The method according to claim 33 further comprising the step of identifying at least one of a start and a stop position of the region of interest within the second set of images.

35. The method according to claim 33 wherein the step of processing the first and second set of images comprises identifying, in the first set of images and the second set of images, a feature selected from the group consisting of pathological landmarks, anatomical landmarks, sizes of anatomical features, diameter of a lumen, bifurcations of a vascular anatomy, a shape of a vessel border, and a combination thereof.

36. The method according to claim 33 wherein the step of processing the first and second set of images comprises cross-correlating at least a portion of the first set of images and the second set of images.

37. The method according to claim 33 wherein the step of processing the first and second set of images comprises processing three-dimensional image data.

38. The method according to claim 32 wherein the second imaging modality is selected from the group consisting of OCT, angiography, angioscopy, NIR spectroscopy, Raman spectroscopy, IVUS, radio-frequency IVUS, elastography, sono-luminescent imaging, microbubble enhanced IVUS, targeted microbubble enhanced IVUS, fluorescence spectroscopy, and photo-acoustic imaging.

39. The method according to claim 32 further comprising the step of processing the second set of images in real-time to determine a measure of a quality of the second set of images, and controlling the medium displacement operation to improve the quality.

40. The method according to claim 32 further comprising the steps of:
identifying when suboptimal imaging data has been acquired using the second imaging modality and determining that a fault has occurred.

41. The method according to claim 40 further comprising the steps of:
reversing a direction of translation of the functional component of the imaging probe until a region that corresponded to the fault has been traversed, and;
directing an additional medium displacement operation while an additional translation operation is performed over the region corresponding to the fault; and
obtaining additional images from the second imaging modality while the additional medium displacement operation is performed, and wherein the additional images are spatially correlated with a relative position of the imaging probe.

42. The method according to claim 1 wherein the medium displacement operation comprises the step of providing a flushing solution including a contrast medium, wherein the method further comprises the step of determining an adequacy of the medium displacement operation using an external imaging modality.

43. The method according to claim 42 wherein the external imaging modality comprises angiography.

44. The method according to claim 32 wherein the first imaging modality and the second imaging modality employ the same form of imaging energy.

45. The method according to claim 1 wherein at least one of the first translation operation and the second translation operation include a pullback operation.

46. The method according to claim 1 wherein at least one of the first translation operation and the second translation operation includes a push-forward operation.

47. The method according to claim 1 wherein the speed of one or more of the first translation operation and the second translation operation are configured for an associated imaging modality.

48. The method according to claim 47, wherein the speed of the second translation operation is faster than the speed of the first translation operation.

49. The method according to claim 1 wherein the imaging probe is positioned within a lumen.

50. The method according to claim 49 wherein the lumen is an interior of a blood vessel.

51. The method according to claim 1 further comprising the step of disabling the first imaging modality while performing the minimally invasive procedure.

52. The method according to claim 1 further comprising the step of providing an image acquisition triggering signal to an external imaging apparatus during one or more of the first translation operation and the second translation operation for correlating acquisition of images obtained by the external imaging apparatus with an associated position of the functional component of the imaging probe.

53. The method according to claim 52 wherein the image acquisition triggering signal is provided according to a preselected time interval.

54. The method according to claim 52 wherein the image acquisition triggering signal is provided at time intervals related one or more of the initiation of a medium displacement operation, the termination of a medium displacement operation, and time points when the imaging probe is imaging a region of interest.

55. The method according to claim 1 wherein the functional component of the imaging probe is an imaging assembly.

56. A method of directing a medium displacement operation for performing a minimally invasive imaging procedure within a lumen or cavity, the method comprising the steps of:
a) obtaining one or more images from a first imaging modality of an imaging probe, wherein the first imaging modality is compatible with a presence of a displaceable medium;
b) processing the one or more images to identify a region of interest; and c) if a region of interest is identified, directing a medium displacement operation and performing a minimally invasive procedure within the region of interest while the medium displacement operation is performed.

57. The method according to claim 56 wherein the minimally invasive procedure is improved by the medium displacement operation.

58. The method according to claim 56 further comprising the step of spatially correlating the one or more images with a relative position of the imaging probe.

59. The method according to claim 56 wherein the step of obtaining the one or more images includes obtaining forward-looking images in a forward-looking direction, and wherein the step of processing the one or more images further includes processing the forward-looking images to determine if a position in a forward-looking direction of the imaging probe is a region of interest.

60. The method according to claim 59 further comprising the step of translating a functional component of the imaging probe to the position in the forward-looking direction prior to the step of directing the medium displacement operation and performing the minimally invasive procedure.

61. The method according to claim 59 wherein the minimally invasive procedure includes obtaining one or more images from an additional forward looking imaging modality in a forward looking direction.

62. The method according to claim 61 wherein the step of obtaining one or more images in a forward looking direction according to one or both of the first imaging modality and the additional forward looking imaging modality is performed by controlling an orientation of a movable member within an imaging assembly of the imaging probe for deflecting imaging energy in the forward looking direction.

63. The method according to claim 56 further comprising the steps of:
d) translating a functional component of the imaging probe to a new position, and
e) repeating steps a) through c).

64. The method according to claim 63 wherein the new position is adjacent to the current position.

65. The method according to claim 63 wherein when a given position is determined to be a region of interest, the medium displacement operation is continued until a subsequent position is no longer determined to be a region of interest.

66. The method according to claim 63 wherein the step of translating the functional component of the imaging probe includes moving the functional component of the imaging probe in a forward direction.

67. The method according to claim 56 wherein a functional component of the imaging probe is translated while performing any one or more of steps a), b) and c).

68. The method according to claim 67 further comprising repeating steps a) through c) one or more times.

69. The method according to claim 56 wherein the imaging probe includes an additional imaging modality compatible with a presence of the displaceable medium, the method further comprising the steps of:
obtaining an additional set of images from the additional imaging modality; and
further processing the additional set of images to identify a region of interest.

70. The method according to claim 56 wherein the minimally invasive procedure is a therapeutic procedure.

71. The method according to claim 56 further comprising the step of terminating the medium displacement operation prior to translating a functional component of the imaging probe to a new position.

72. The method according to claim 56 wherein the step of directing the medium displacement operation includes automating the medium displacement operation.

73. The method according to claim 72 wherein the medium displacement operation is automated after receiving an input from a user authorizing the medium displacement operation.

74. The method according to claim 72 wherein the step of automating the medium displacement operation includes controlling a medium displacement apparatus to perform the medium displacement operation.

75. The method according to claim 74 wherein the medium displacement apparatus includes a fluid delivery apparatus.

76. The method according to claim 75 wherein the fluid delivery apparatus further comprises a component selected from the group consisting of an auto-injector, pressure infuser bag, peristaltic pump, syringe pump, piston pump, valved system, gravity pressurized system, and a means for the external application of pressure.

77. The method according to claim 56 further comprising the step of monitoring a parameter related to the medium displacement operation.

78. The method according to claim 77 further comprising one of alerting an operator and terminating the medium displacement operation when the parameter does not lie within a pre-determined range of values.

79. The method according to claim 56 wherein the step of processing one or more images obtained from the first imaging modality further comprises processing images obtained in a spatial region preceding a current position of the imaging probe.

80. The method according to claim 56 wherein the step of processing the one or more images obtained from the first imaging modality includes processing three-dimensional image data.

81. The method according to claim 56 wherein the step of identifying the region of interest includes comparing the one or more images obtained from the first imaging modality to known or expected properties.

82. The method according to claim 81 wherein the step of comparing the one or more images obtained from the first imaging modality to known or expected properties comprises computing a comparison metric and comparing the comparison metric with a threshold value.

83. The method according to claim 82 wherein the threshold value is configurable by an operator.

84. The method according to claim 81 wherein the known or expected properties are spatial profiles and/or tissue types of one or more of normal anatomical features, pathological anatomical features, and medical implants.

85. The method according to claim 56 wherein the step of processing the one or more images obtained from the first imaging modality includes one of determining a spatial profile of a detected border, a tissue type, and a temperature profile.

86. The method according to claim 85 wherein the step of determining a tissue type comprises performing a method selected from the group consisting of grayscale pixel analysis, radiofrequency analysis, texture analysis, and heuristic analysis.

87. The method according to claim 85 wherein the first imaging modality is IVUS, and wherein the step of determining a tissue type comprises analysis of radio-frequency properties of a backscattered ultrasound signal.

88. The method according to claim 56 wherein the step of processing the one or more images obtained from the first imaging modality includes executing a pattern recognition algorithm.

89. The method according to claim 56 wherein the region of interest includes a substance or feature selected from the group consisting of plaque, thrombus, branch points, lesions, calcifications, stents, brachytherapy implants, stenoses, areas of vessel wall thickening, lipid cores, necrotic regions, fibrous caps, dissections, microbubbles, targeted microbubbles, vascular lesions, and a combination thereof.

90. The method according to claim 56 wherein the region interest is associated with indeterminate results obtained by processing of the one or more images obtained from the first imaging modality.

91. The method according to claim 56 wherein the first imaging modality is selected from the group consisting of grayscale IVUS, radio-frequency IVUS, Virtual Histology™, integrated backscatter, iMap™, elastography, NIR spectroscopy, sono-luminescent imaging, microbubble enhanced IVUS, targeted microbubble enhanced IVUS, photo-acoustic imaging, fluorescence spectroscopy, biosensors, and ion-selective field effect transistors.

92. The method according to claim 56 wherein the minimally invasive procedure includes obtaining one or more images from a second imaging modality.

93. The method according to claim 92 further comprising the step of processing the one or more images obtained from the first imaging modality and one or more images obtained from the second imaging modality to spatially correlate one or more images obtained from the first imaging modality with the one or more images obtained from the second imaging modality.

94. The method according to claim 93 wherein the step of processing the one or more images obtained from the first imaging modality and the one or more images obtained from the second imaging modality includes identifying, in the one or more images obtained from the first imaging modality and the one or more images obtained from the second imaging modality, a feature selected from the group consisting of pathological landmarks, anatomical landmarks, sizes of anatomical features, diameter of a lumen, bifurcations of a vascular anatomy, a shape of a vessel border, and a combination thereof.

95. The method according to claim 93 wherein the step of processing the one or more images obtained from the first imaging modality and the one or more images obtained from the first imaging modality includes cross-correlating at least a portion of the one or more images obtained from the first imaging modality and the one or more images obtained from the second imaging modality.

96. The method according to claim 93 wherein the step of processing the one or more images obtained from the first imaging modality and the one or more images obtained from the second imaging modality includes processing three-dimensional image data.

97. The method according to claim 92 wherein the second imaging modality is selected from the group consisting of OCT, angiography, angioscopy, NIR spectroscopy, Raman spectroscopy, IVUS, radio-frequency IVUS, elastography, sono-luminescent imaging, microbubble enhanced IVUS, targeted microbubble enhanced IVUS, fluorescence spectroscopy, and photo-acoustic imaging.

98. The method according to claim 92 further comprising the step of processing the one or more images obtained from the second imaging modality in real-time to determine a measure of a quality of the one or more images obtained from the second imaging modality.

99. The method according to claim 98 further comprising controlling the medium displacement operation to improve the quality.

100. The method according to claim 92 wherein the first imaging modality and the second imaging modality employ the same form of imaging energy.

101. The method according to claim 56 imaging probe is positioned within a lumen.

102. The method according to claim 101 wherein the lumen is an interior of a blood vessel.

103. The method according to claim 98 further comprising the steps of:
   identifying when suboptimal imaging data has been acquired using the second imaging modality and providing a notification that a fault has occurred; and
   obtaining an additional set of images using the second imaging modality.

104. The method according to claim 56 further comprising the step of providing an image acquisition triggering signal to an external imaging apparatus during one or more of the first translation operation and the second translation operation for correlating acquisition of images obtained by the external imaging apparatus with the relative position of the imaging probe.

105. The method according to claim 104 wherein the image acquisition triggering signal is provided according to a preselected time interval.

106. The method according to claim 104 wherein the image acquisition triggering signal is provided at time intervals related one or more of the initiation of a medium displacement operation, the termination of a medium displacement operation, and time points when the imaging probe is imaging a region of interest.

107. A method of directing a medium displacement operation for performing a minimally invasive procedure within a lumen or cavity with a probe, the method comprising the steps of:
   obtaining, with an external imaging apparatus, one or more images of a region within which the minimally invasive procedure is to be performed;
   identifying a region of interest within the one or more images;
   translating a functional component of the probe to the region of interest while obtaining one or more additional images with the external imaging apparatus, wherein a position of the functional component is identifiable in the one or more additional images; and
   directing a medium displacement operation while performing a translation operation associated with the functional component of the probe within the region of interest.

108. The method according to claim 107 further comprising the step performing the minimally invasive procedure within the region of interest during the medium displacement operation.

109. The method according to claim 107 wherein the functional component of the probe includes a fiducial marker identifiable by the external imaging apparatus.

110. The method according to claim 109 wherein an imaging modality of the external imaging apparatus is fluoroscopy, and wherein the fiducial marker is a radiopaque marker.

111. The method according to claim 107 further comprising the step of directing an additional medium displacement operation during the step of obtaining the one or more images with the external imaging apparatus.

112. The method according to claim 107 wherein the probe is positioned within a lumen.

113. The method according to claim 112 wherein the lumen is an interior of a blood vessel.

114. A method of directing a medium displacement operation for performing a minimally invasive procedure within a lumen or cavity, the method comprising the steps of:
obtaining a set of measurements from a non-imaging detection modality when a first translation operation of a functional component of a probe is performed;
spatially correlating the set of measurements with an associated position of the functional component of the probe, wherein the non-imaging detection modality is compatible with a presence of a displaceable medium;
processing the set of measurements and identifying a region of interest; and
directing a medium displacement operation while a second translation operation of the functional component of the probe is performed over the region of interest;
wherein the minimally invasive procedure is performed within the region of interest during the medium displacement operation.

115. A method of directing a medium displacement operation for performing a minimally invasive imaging procedure within a lumen or cavity, the method comprising the steps of:
a) obtaining one or more measurements from a non-imaging detection modality of a probe, wherein the non-imaging detection modality is compatible with a presence of a displaceable medium;
b) processing the one or more measurements to identify a region of interest; and
c) if a region of interest is identified, directing a medium displacement operation and performing a minimally invasive procedure while the medium displacement operation is performed.

116. The method according to claim 115 further wherein the non-imaging detection modality is selected from the group consisting of thermography and sensing a biological analyte.

117. The method according to claim 115 further comprising the steps of:
d) translating a functional component of the probe to a new position, and
e) repeating steps a) through c).

118. The method according to claim 117 wherein the non-imaging detection modality is selected from the group consisting of thermography and sensing a biological analyte.

119. The method according to claim 117 wherein the new position is adjacent to the current position.

120. The method according to claim 117 wherein when a given position is determined to be a region of interest, the medium displacement operation is continued until a subsequent position is no longer determined to be a region of interest.

121. The method according to claim 117 wherein the step of translating the functional component of the probe includes moving the functional component of the probe in a forward direction.

122. The method according to claim 115 wherein a functional component of the probe is translated while performing any one or more of steps a), b) and c).

123. The method according to claim 122 further comprising repeating steps a) through c) one or more times.

124. A system for performing a minimally invasive procedure within a lumen or cavity, the system comprising:
an imaging probe configured for insertion into a lumen or cavity, said imaging probe including an imaging assembly configured to obtain images according to a first imaging modality, wherein said first imaging modality is compatible with a presence of a displaceable medium within the lumen or cavity, and wherein said imaging probe includes a functional component for performing the minimally invasive procedure;
a medium displacement means for effecting a displacement of the displaceable medium within the lumen or cavity;
at least one processor in communication with said imaging assembly, wherein said processor is configured to:
spatially correlate a first set of images with an associated position of said functional component, wherein the first set of images are obtained from said first imaging modality during a first translation operation of said functional component;
process the first set of images to identify a region of interest; and
direct a medium displacement operation employing said medium displacement means while a second translation operation of said functional component is performed over the region of interest;
such that the minimally invasive procedure may be performed within the region of interest during the medium displacement operation.

125. A system for performing a minimally invasive procedure within a lumen or cavity, the system comprising:
an imaging probe configured for insertion into a lumen or cavity, said imaging probe including an imaging assembly configured to obtain images according to a first imaging modality, wherein said first imaging modality is compatible with a presence of a displaceable medium within the lumen or cavity, and wherein said imaging probe includes a functional component for performing the minimally invasive procedure;
a medium displacement means for effecting a displacement of the displaceable medium within the lumen or cavity;
at least one processor in communication with said imaging assembly of said imaging probe, wherein said processor is configured to:
spatially correlate a first set of images with an associated position of said functional component;
process the first set of images to identify a region of interest; and
direct a medium displacement operation employing said medium displacement means while the minimally invasive procedure is performed within the region of interest.

126. A system for performing a minimally invasive procedure within a lumen or cavity, the system comprising:
a probe configured for insertion into a lumen or cavity, said probe including a functional component for performing the minimally invasive procedure;
an external imaging apparatus configured to provide images of said lumen or cavity;
a medium displacement means for effecting a displacement of a displaceable medium within the lumen or cavity;
at least one processor in communication with said external imaging apparatus, wherein said processor is configured to:
process one or more images obtained from said external imaging apparatus and identify a region of interest within the one or more images; and,
while a translation operation associated with the functional component of the probe is performed;

process one or more additional images obtained from said external imaging apparatus to identify a position of said functional component, and direct a medium displacement operation employing said medium displacement means when said functional component is within said region of interest.

127. A system for performing a minimally invasive procedure within a lumen or cavity, the system comprising:
- a probe including a non-imaging detection modality, wherein said non-imaging detection modality is compatible with a presence of a displaceable medium within the lumen or cavity, and wherein said probe includes a functional component for performing the minimally invasive procedure;
- a medium displacement means for effecting a displacement of the displaceable medium within the lumen or cavity;
- at least one processor in communication with said non-imaging detection modality, wherein said processor is configured to:
- spatially correlate a first set of measurements with an associated position of said functional component, wherein the first set of measurements are obtained from said non-imaging detection modality during a first translation operation of said functional component;
- process the set of measurements and identify a region of interest; and
- direct a medium displacement operation employing said medium displacement means while a second translation operation of the functional component of the probe is performed over the region of interest;

such that the minimally invasive procedure may be performed within the region of interest during the medium displacement operation.

128. A system for performing a minimally invasive procedure within a lumen or cavity, the system comprising:
- a probe including a non-imaging detection modality, wherein said non-imaging detection modality is compatible with a presence of a displaceable medium within the lumen or cavity, and wherein said probe includes a functional component for performing the minimally invasive procedure;
- a medium displacement means for effecting a displacement of the displaceable medium within the lumen or cavity;
- at least one processor in communication with said non-imaging detection modality, wherein said processor is configured to:
- obtain one or more measurements from the non-imaging detection modality;
- process the one or more measurements to identify a region of interest; and
- if a region of interest is identified, direct a medium displacement operation employing said medium displacement means, such that the minimally invasive procedure may be performed within the region of interest during the medium displacement operation.

* * * * *